US005753686A

United States Patent [19]
Marin et al.

[11] Patent Number: 5,753,686
[45] Date of Patent: May 19, 1998

[54] METHOD FOR REPELLING FIRE ANTS AND HORN FLIES AND COMPOSITIONS FOR REPELLING FIRE ANTS AND HORN FLIES AND ACTING AS ANTI-FEEDANTS FOR FIRE ANTS AND HORN FLIES

[75] Inventors: Anna Belle Marin, Long Branch, N.J.; Jerry F. Butler, Gainesville, Fla.

[73] Assignees: International Flavors & Fragrances Inc., N.Y., N.Y.; The University of Florida, Gainesville, Fla.

[21] Appl. No.: 686,470

[22] Filed: Jul. 25, 1996

Related U.S. Application Data

[63] Continuation-in-part of Ser. No. 535,670, Sep. 28, 1995, which is a continuation-in-part of Ser. No. 265,113, Jun. 24, 1994, abandoned, which is a continuation-in-part of Ser. No. 948,142, Sep. 18, 1992, abandoned.

[51] Int. Cl.$^6$ .............................. A01N 31/02; A01N 25/08
[52] U.S. Cl. ........................ 514/739; 514/919; 424/405; 424/409; 424/DIG. 10
[58] Field of Search ............................. 514/739, 919; 424/405, 409, DIG. 10

[56] References Cited

U.S. PATENT DOCUMENTS

| | | | |
|---|---|---|---|
| 3,891,767 | 6/1975 | Kenaga | 514/493 |
| 4,511,552 | 4/1985 | Cox | 424/401 |
| 4,774,082 | 9/1988 | Flashinski et al. | 514/617 |
| 4,855,133 | 8/1989 | Kamei et al. | 424/84 |
| 5,227,406 | 7/1993 | Beldock et al. | 514/703 |
| 5,518,736 | 5/1996 | Magdassi et al. | 424/451 |

FOREIGN PATENT DOCUMENTS 267202  3/1990  Japan.

OTHER PUBLICATIONS

Bartlett, II, *Pesticide Science* 1985, 16(5), pp. 479–487, entitled: "An Olfactometer for Measuring the Repellent Effect of Chemicals on the Stable Fly *Stomoxys calcitrans* (L.)".

Barlett, *Chemical Abstracts*, vol. 104:30390k (1986) [abstract of *Pesticide Science* 1985, 16(5), pp. 479–487].

Harwood and James, "*Entomology in Human and Animal Health*", Seventh Edition, Macmillan Publishing Co., Inc., pp. 430–434 (1977).

King, "Chemicals Evaluated as Insecticides and Repellents at Orlando, Fla.", U.S. Department of Agriculture, Agricultural Research Service, Agriculture Handbook No. 69, pp. 120 and 179 (May 1954).

Beroza and Green, "Materials Tested as Insect Attractants", Agriculture Handbook No. 239, Agricultural Research Service, United States Department of Agriculture, issued Jun. 1963, p. 72.

*Primary Examiner*—John Pak
*Attorney, Agent, or Firm*—Arthur L. Liberman

[57] ABSTRACT

Described is a method for repelling at least one of the insect species:

(i) *Haematobia irritans* (Linnaeus) (commonly known as the horn fly); and (ii) *Solenopsis invicta* Buren (commonly known as the "red imported fire ant")

from a surface or volume inhabited by at least one of said insect species consisting of the step of applying to said surface or said volume a "red imported fire ant" and/or horn fly-repelling quantity and concentration of a geraniol-containing mixture comprising:

(i) from 0 up to about 20% by weight of nerol;

(ii) from about 20 up to about 40% by weight of citronellol; and (iii) from about 50 up to about 70% by weight of geraniol which geraniol-containing mixture is defined according to specific GLC profiles set forth in the figures and refractive index and density set forth in the specification.

10 Claims, 21 Drawing Sheets

FIG.I-A
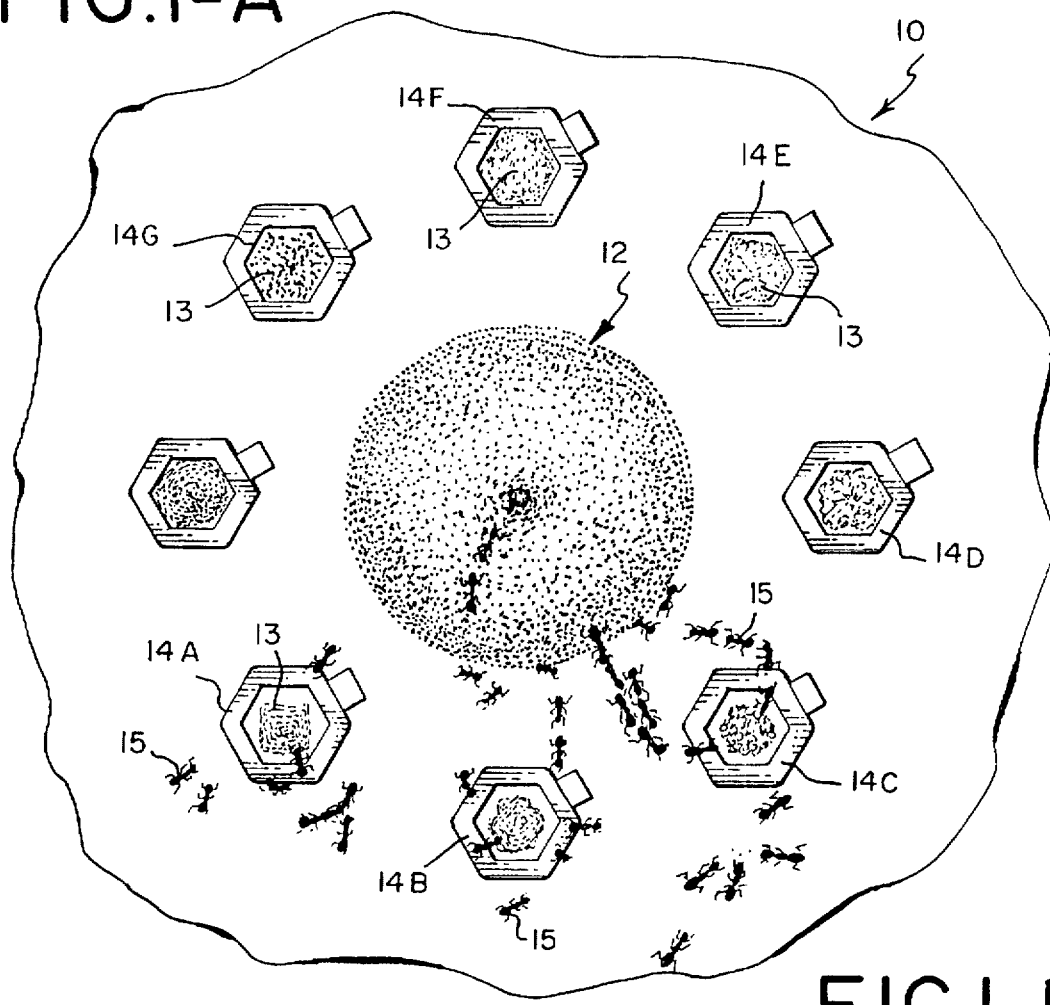
FIG.I-B
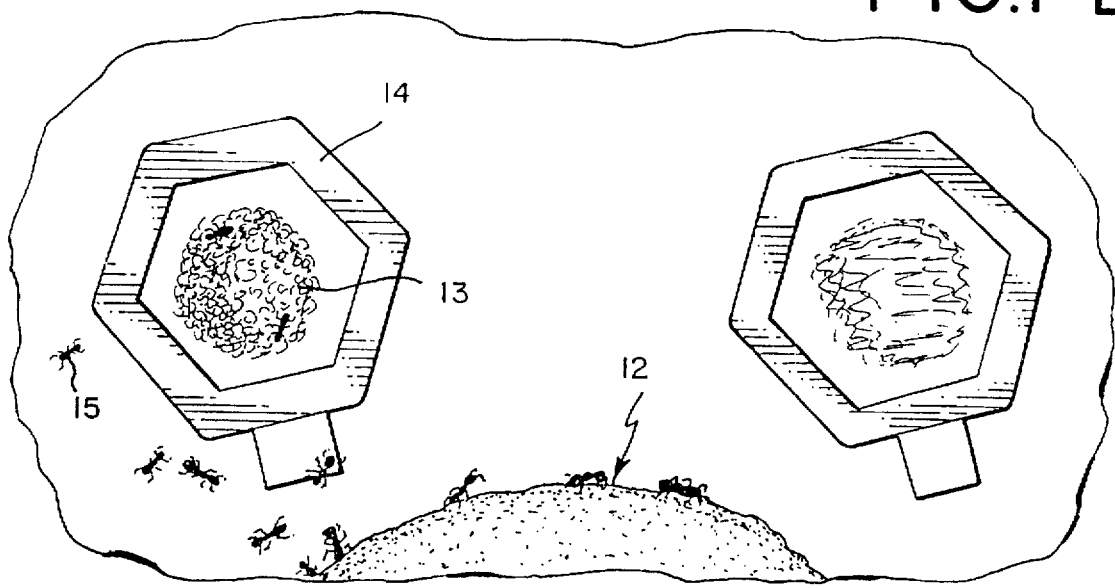

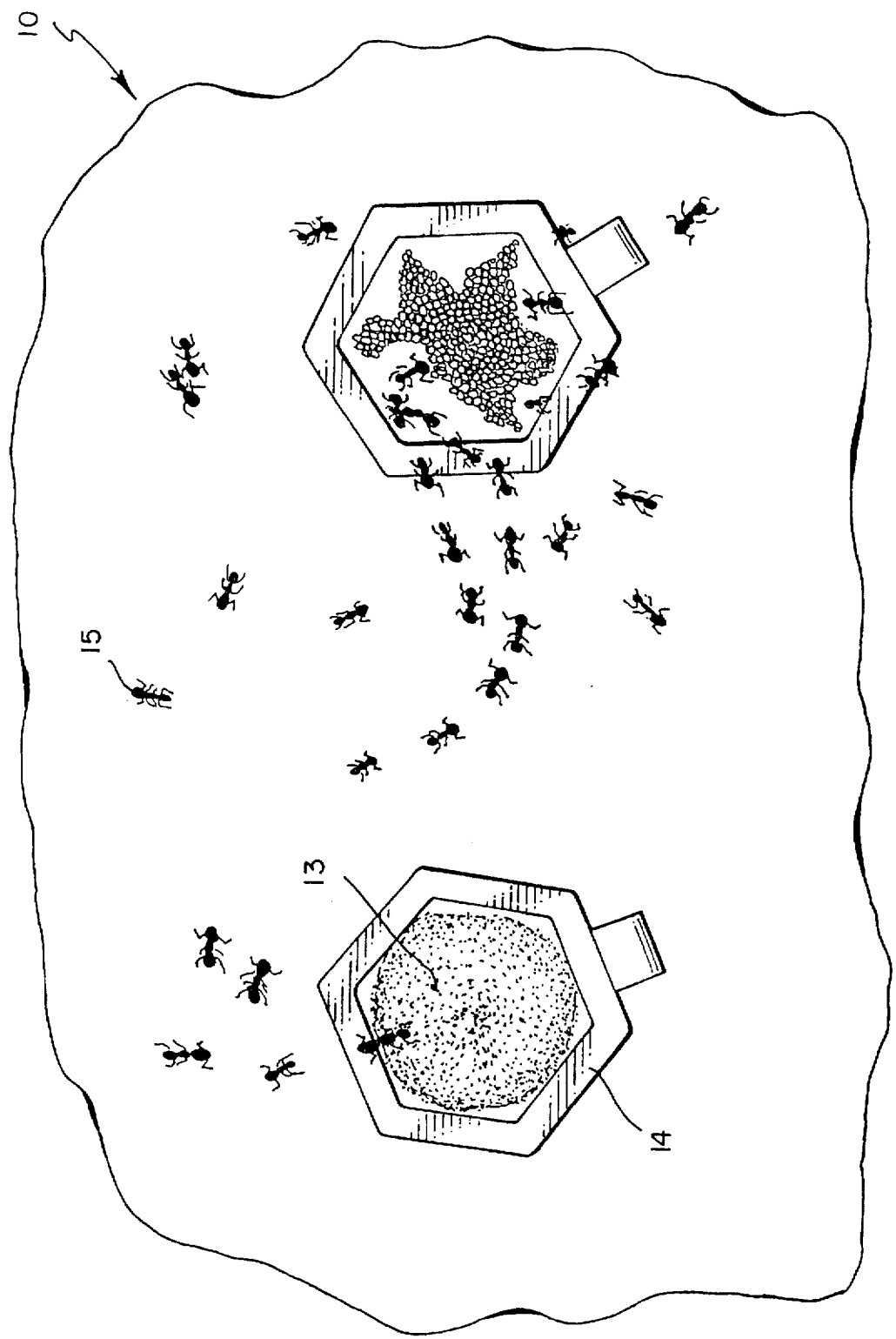
FIG.1-C

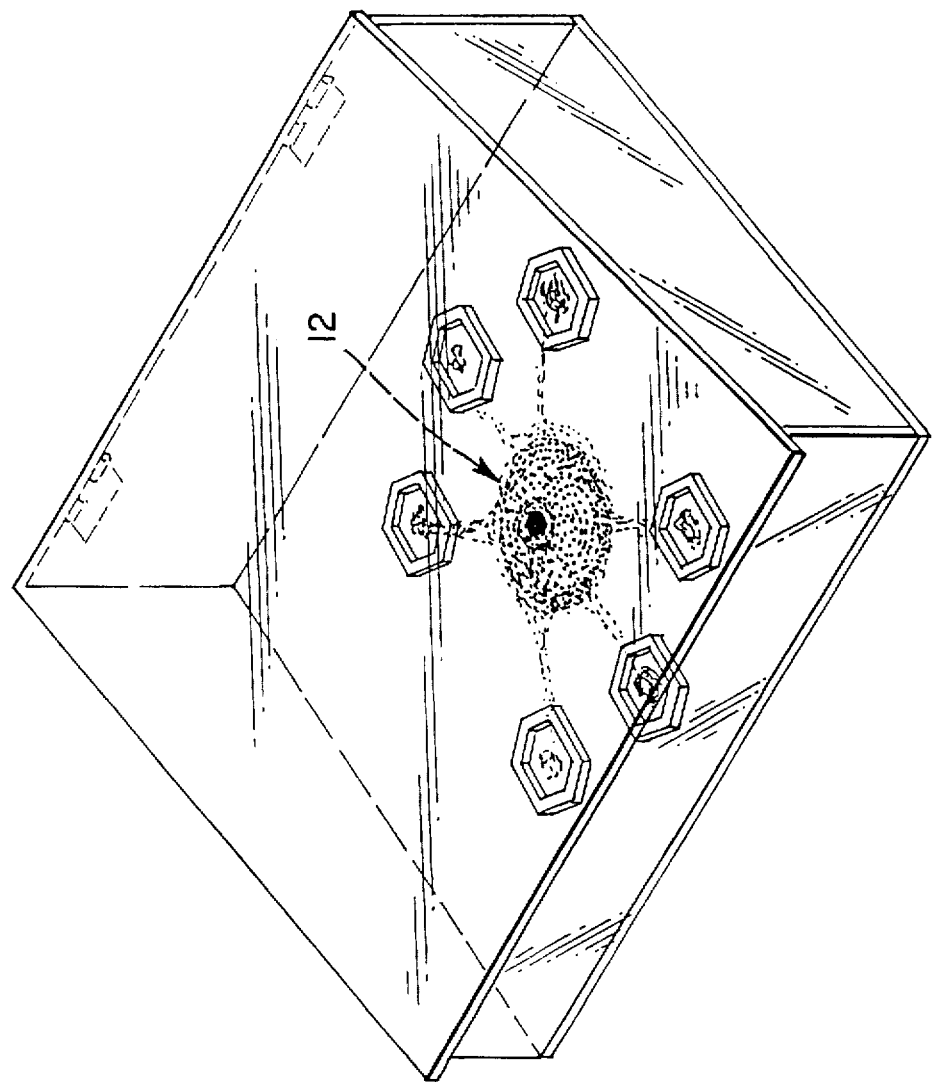
FIG.1-D

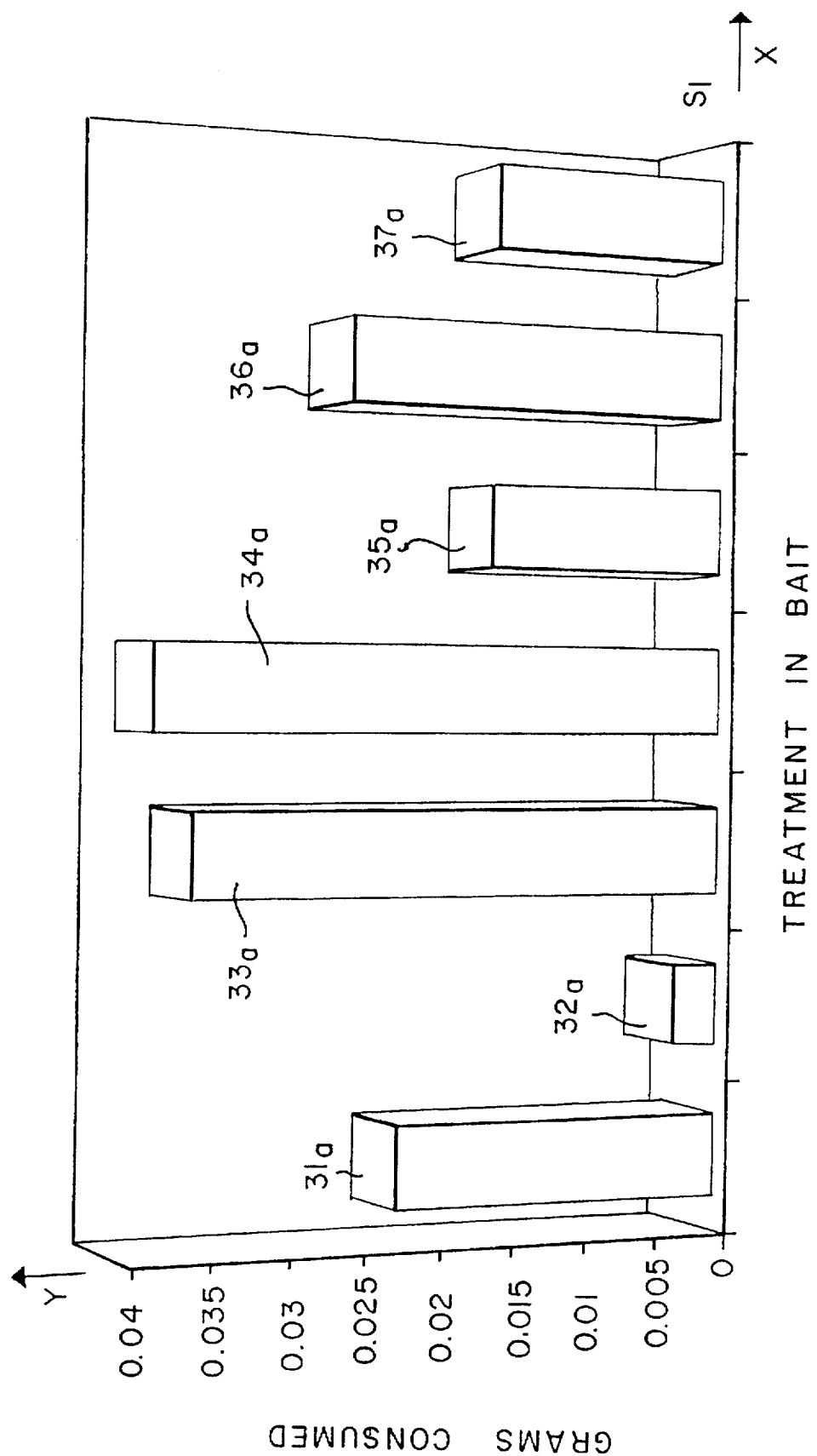

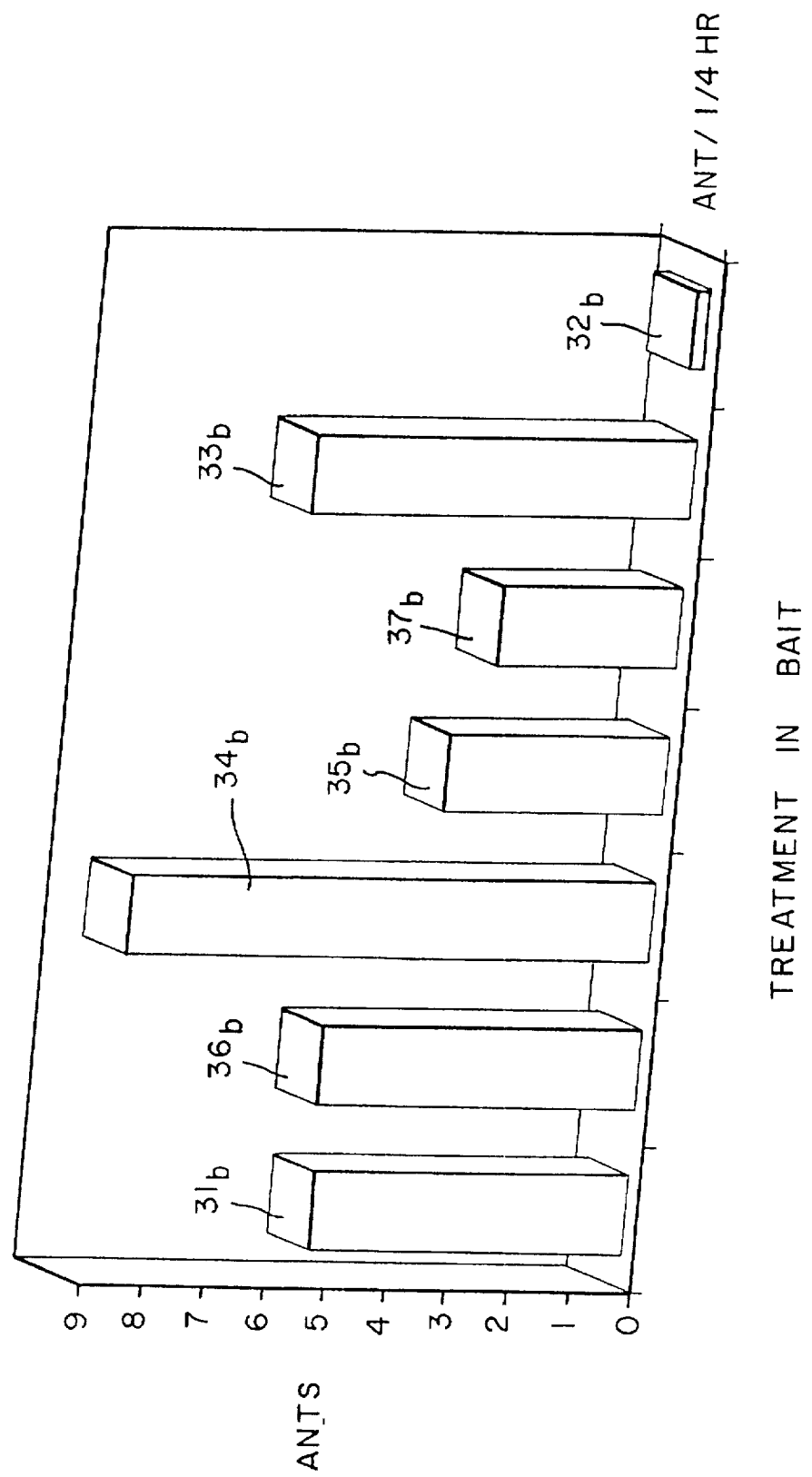
FIG.3-B

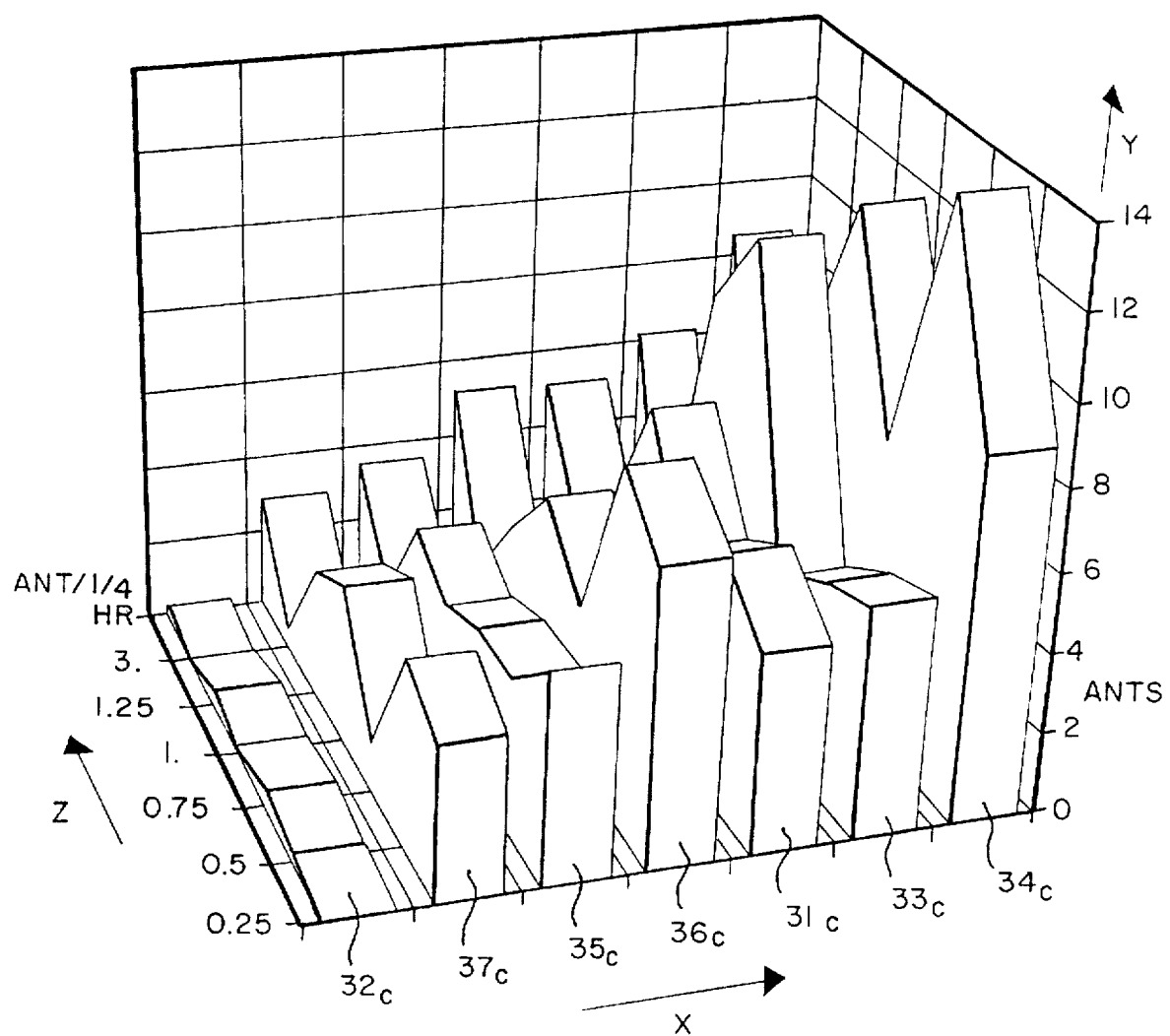

FIG.3-D
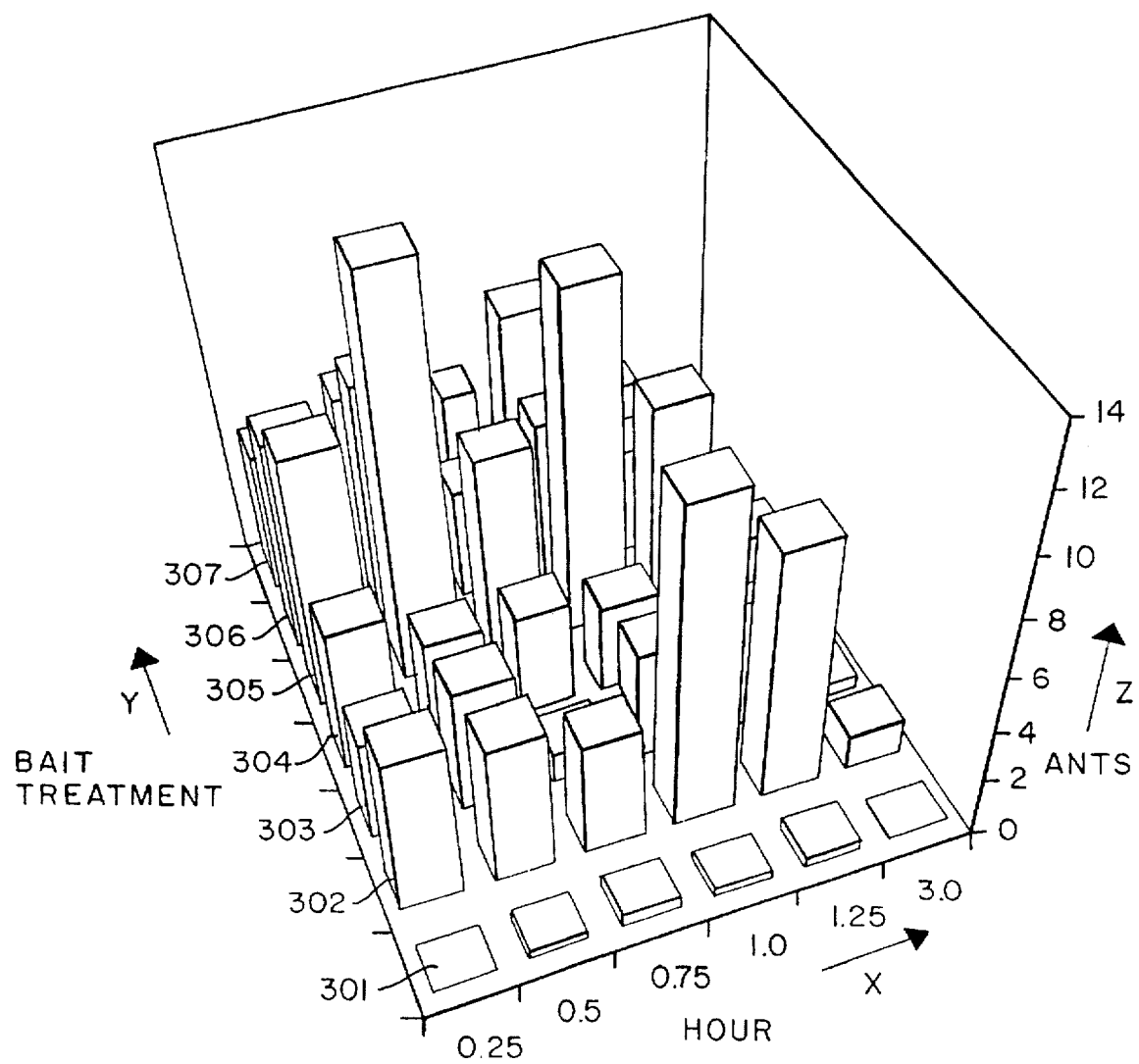

FIG.4-A
FIG.4-B
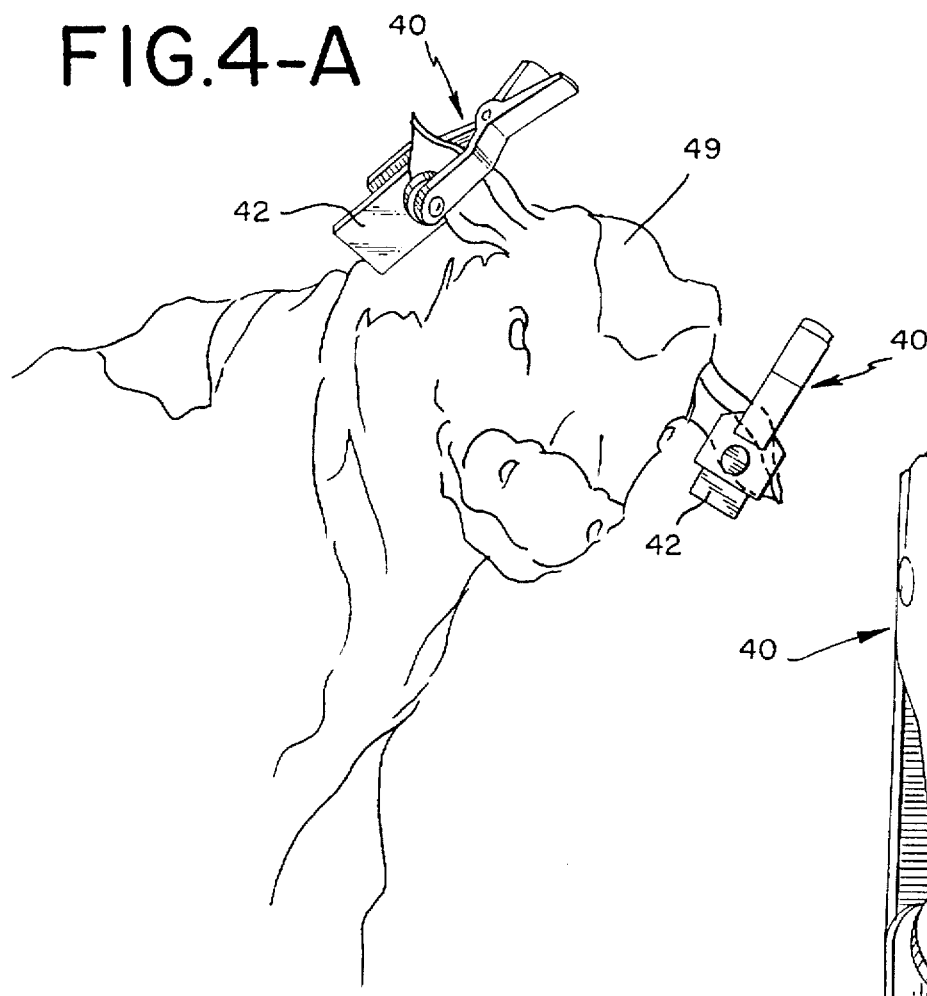

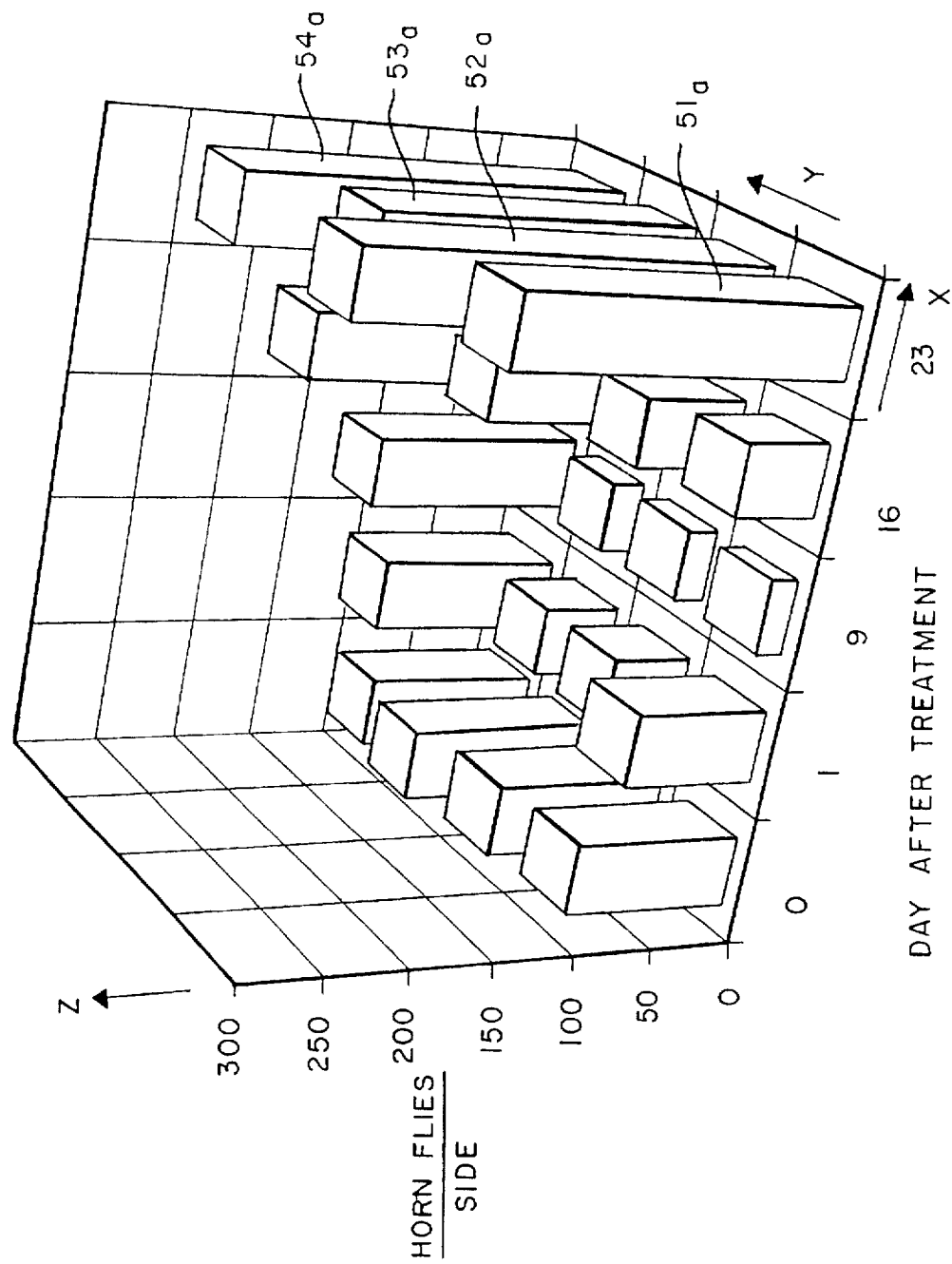

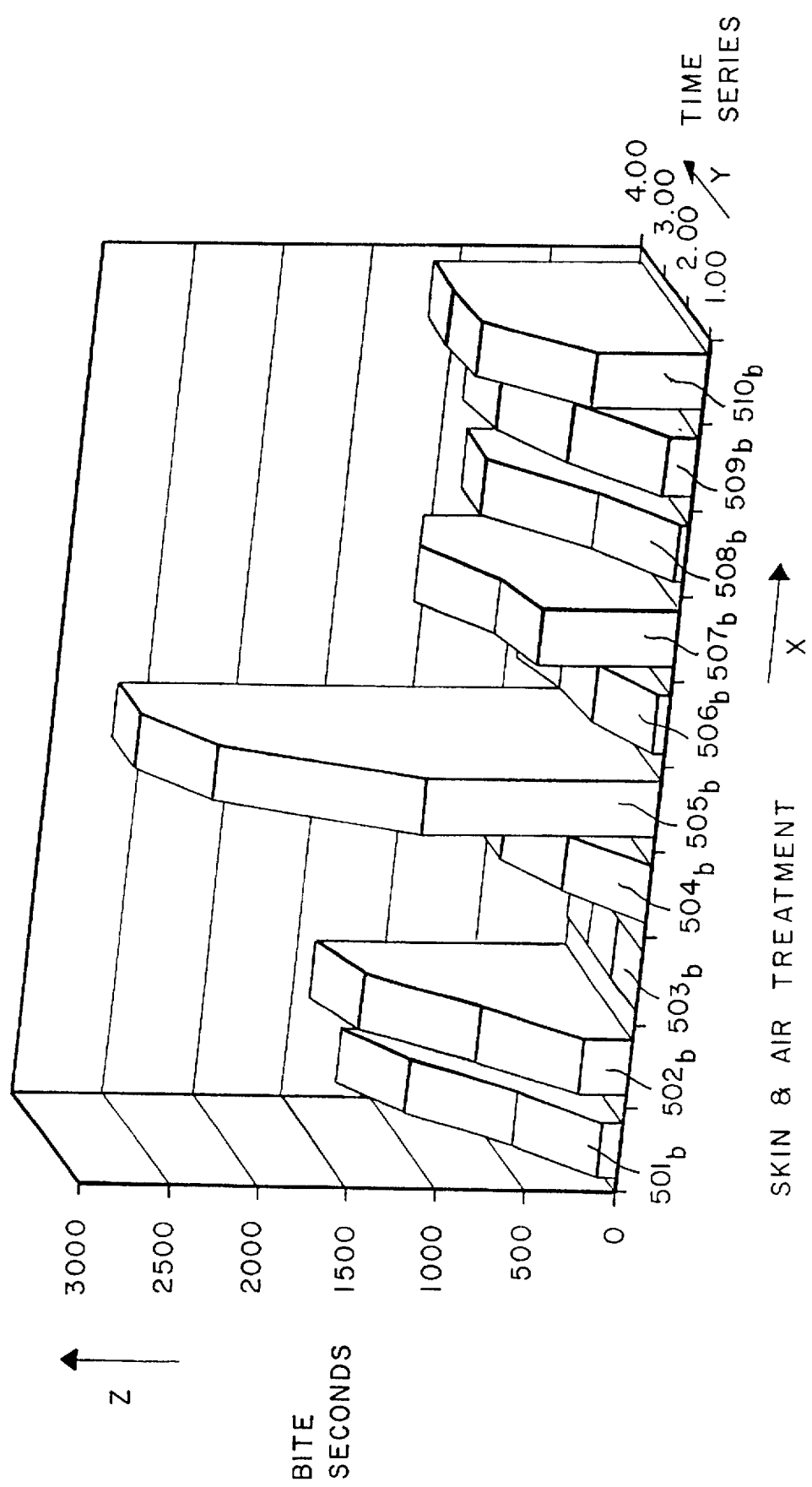
FIG.5-B

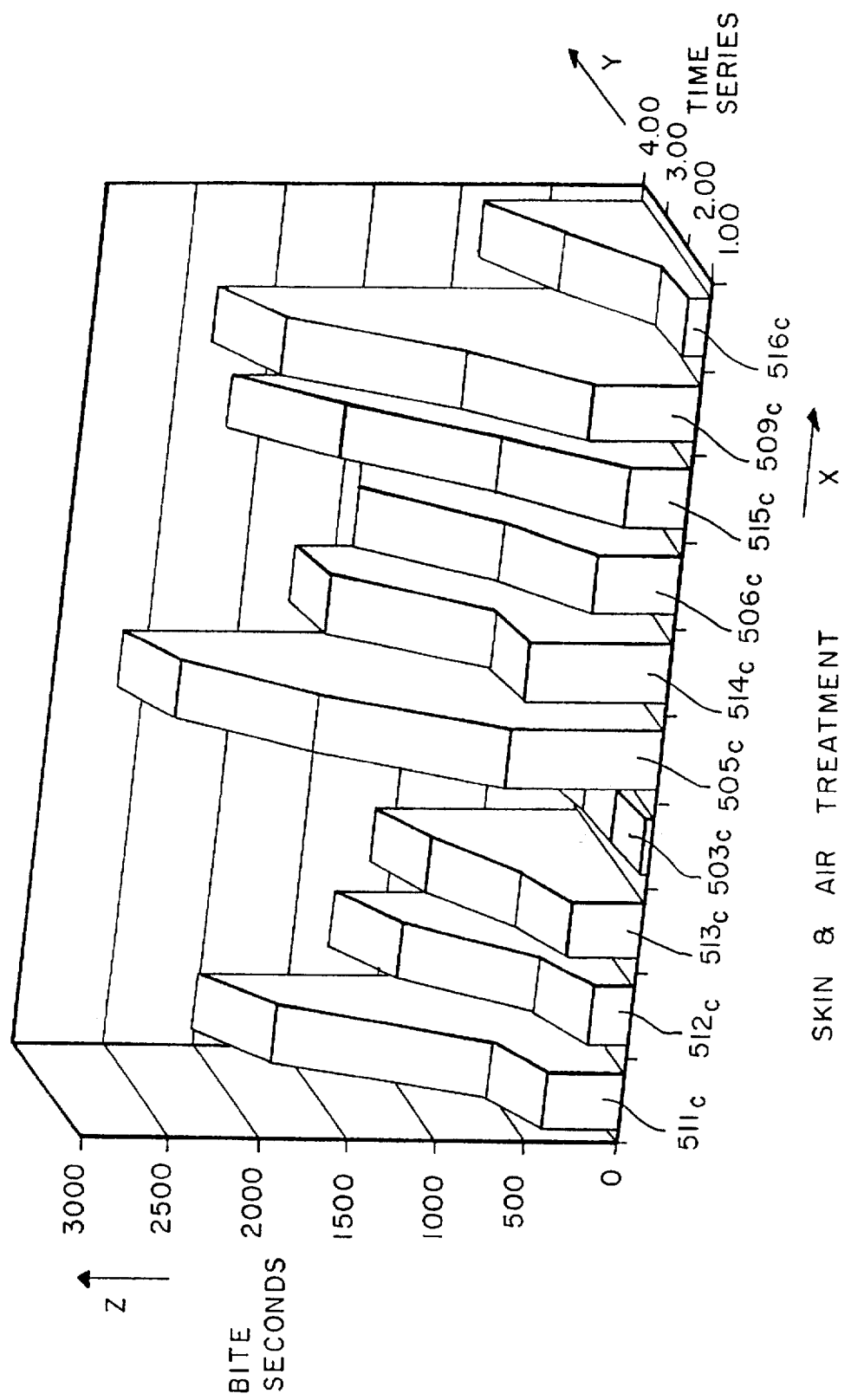

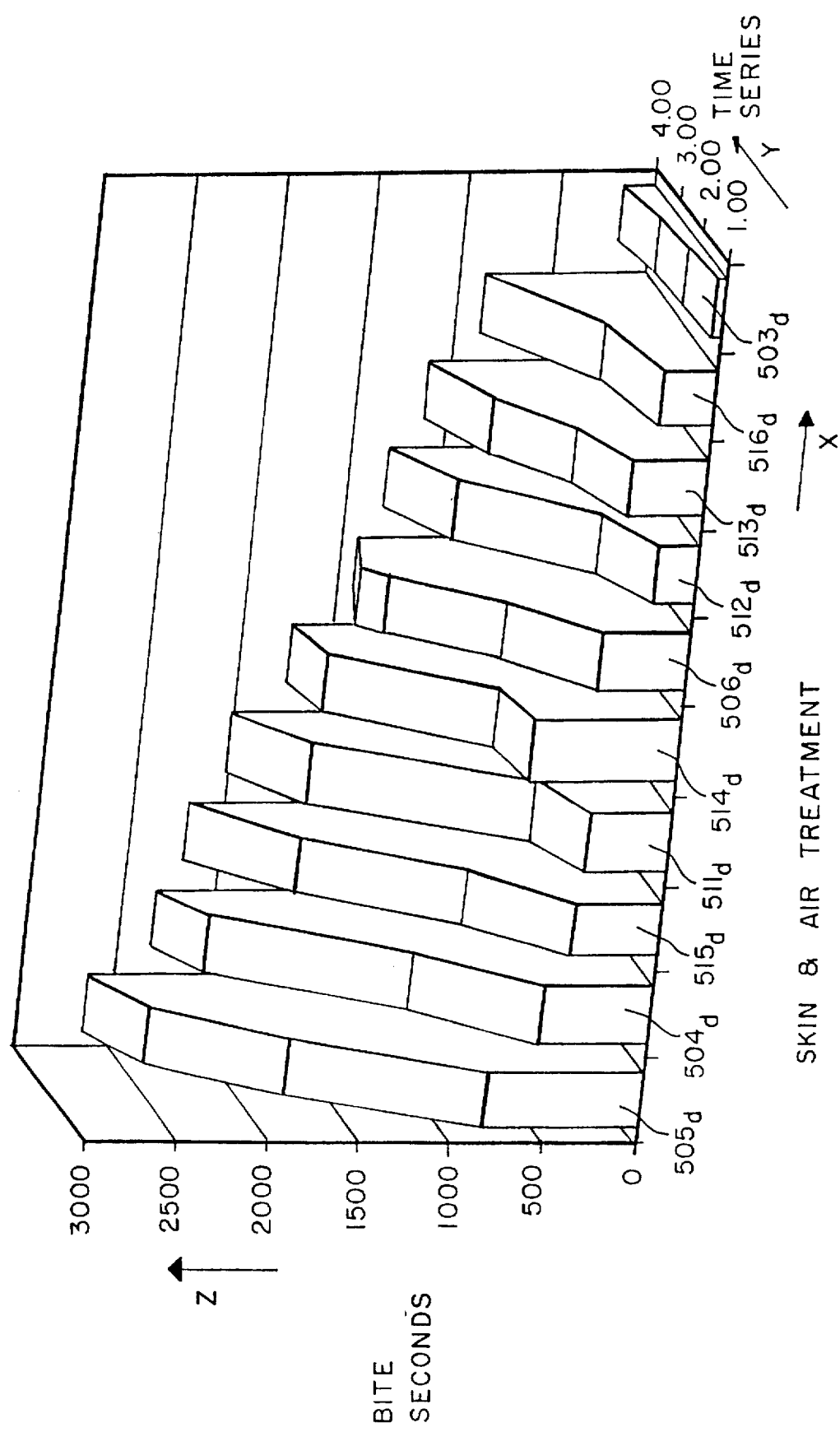

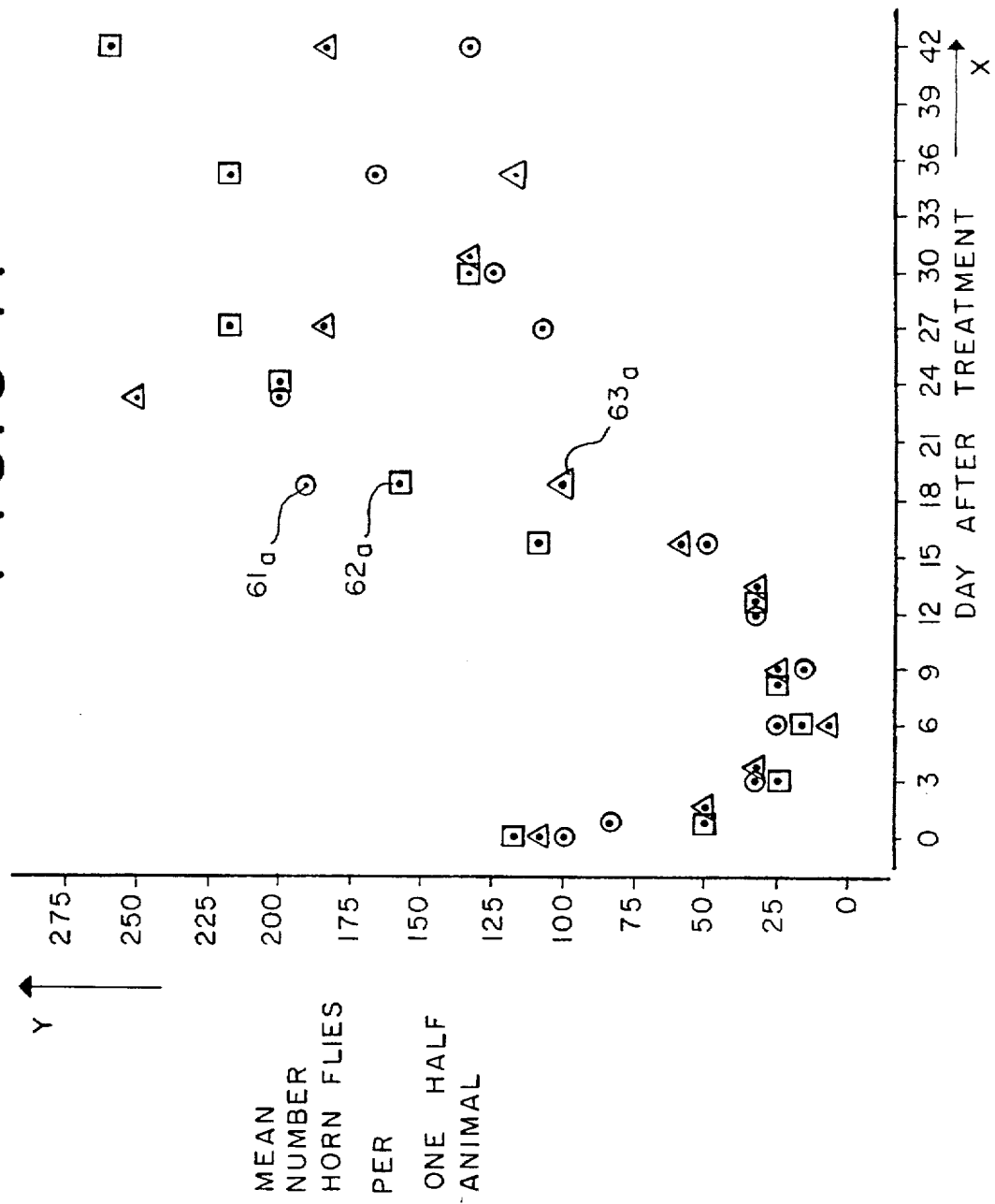

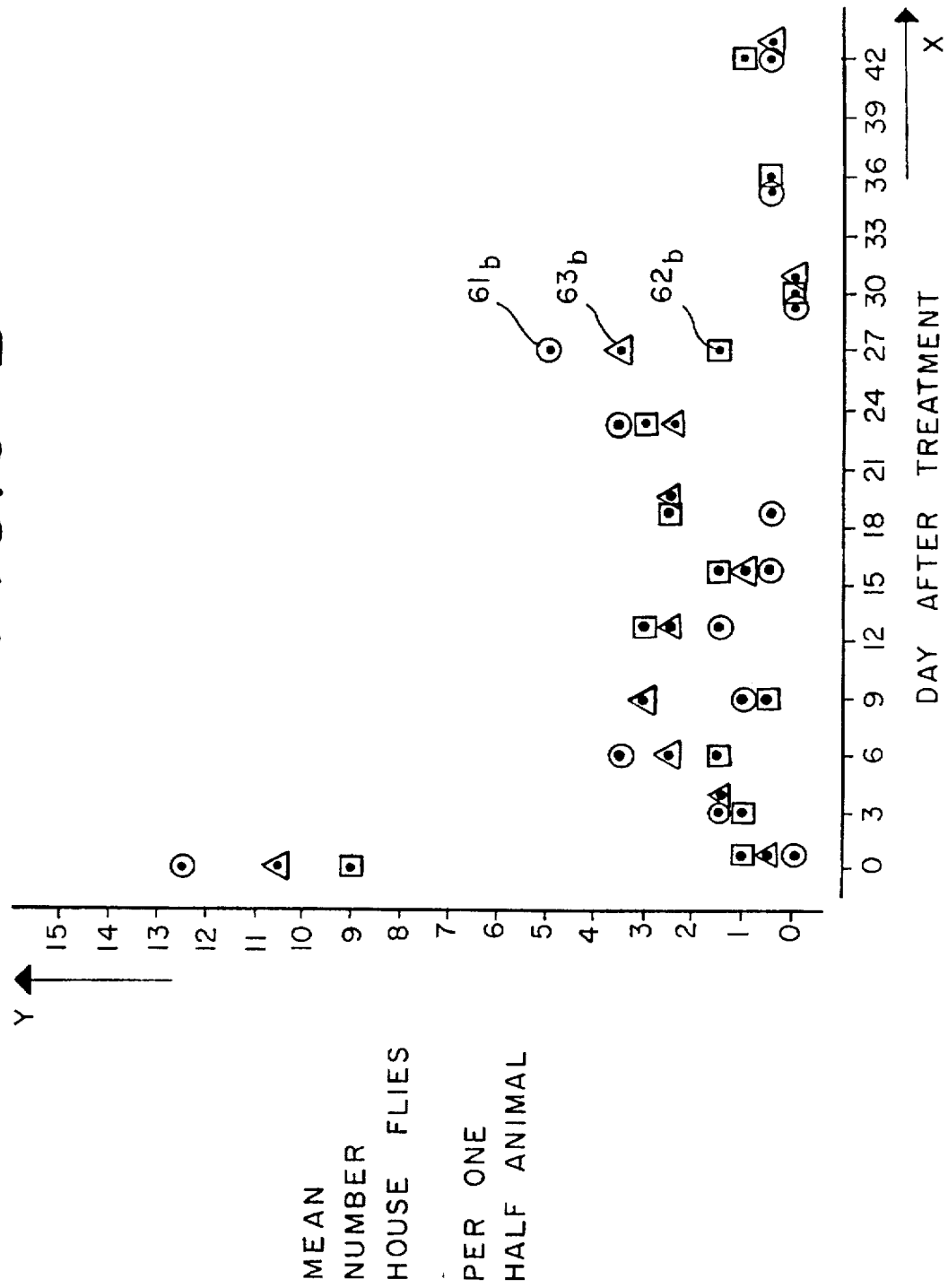

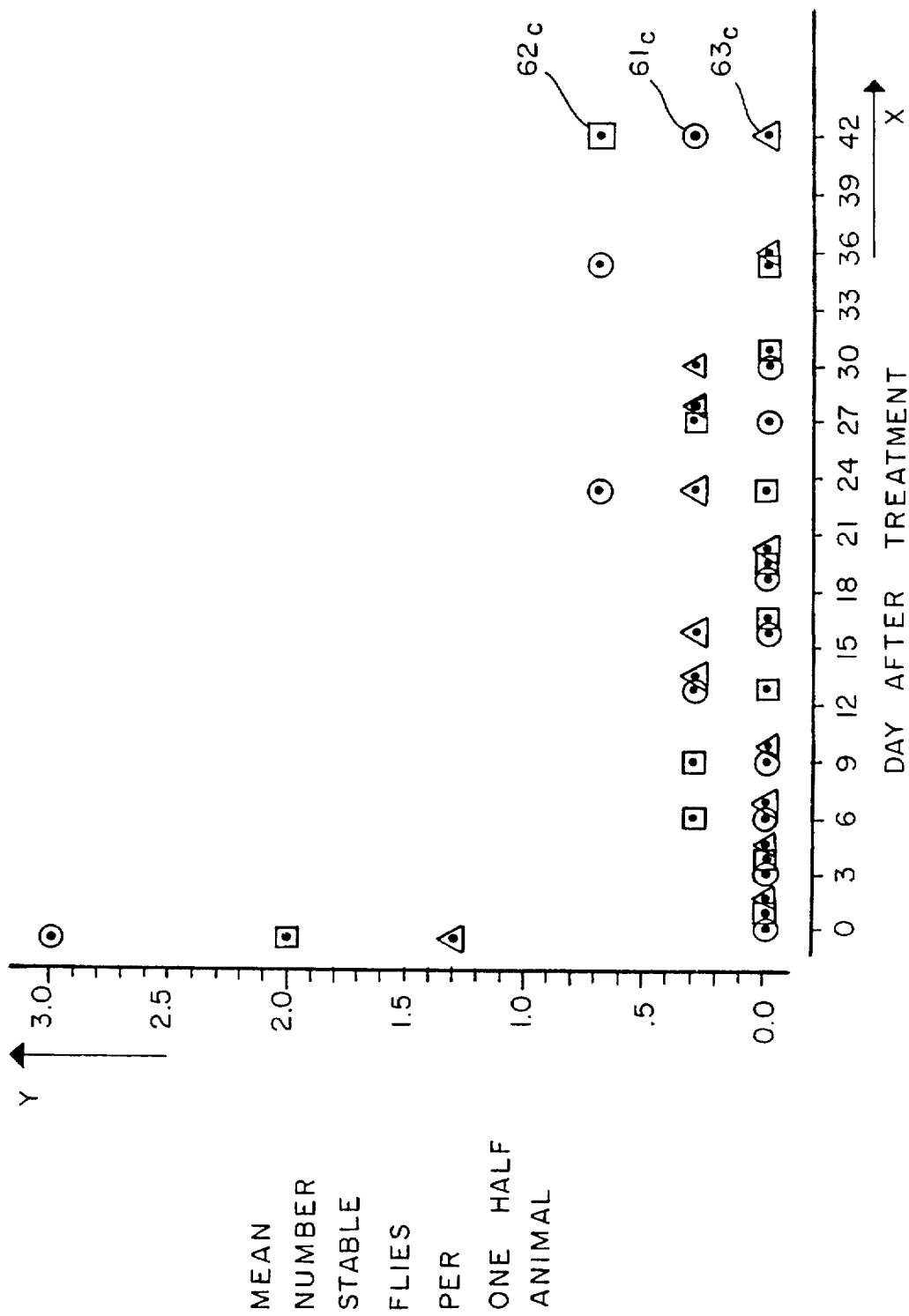

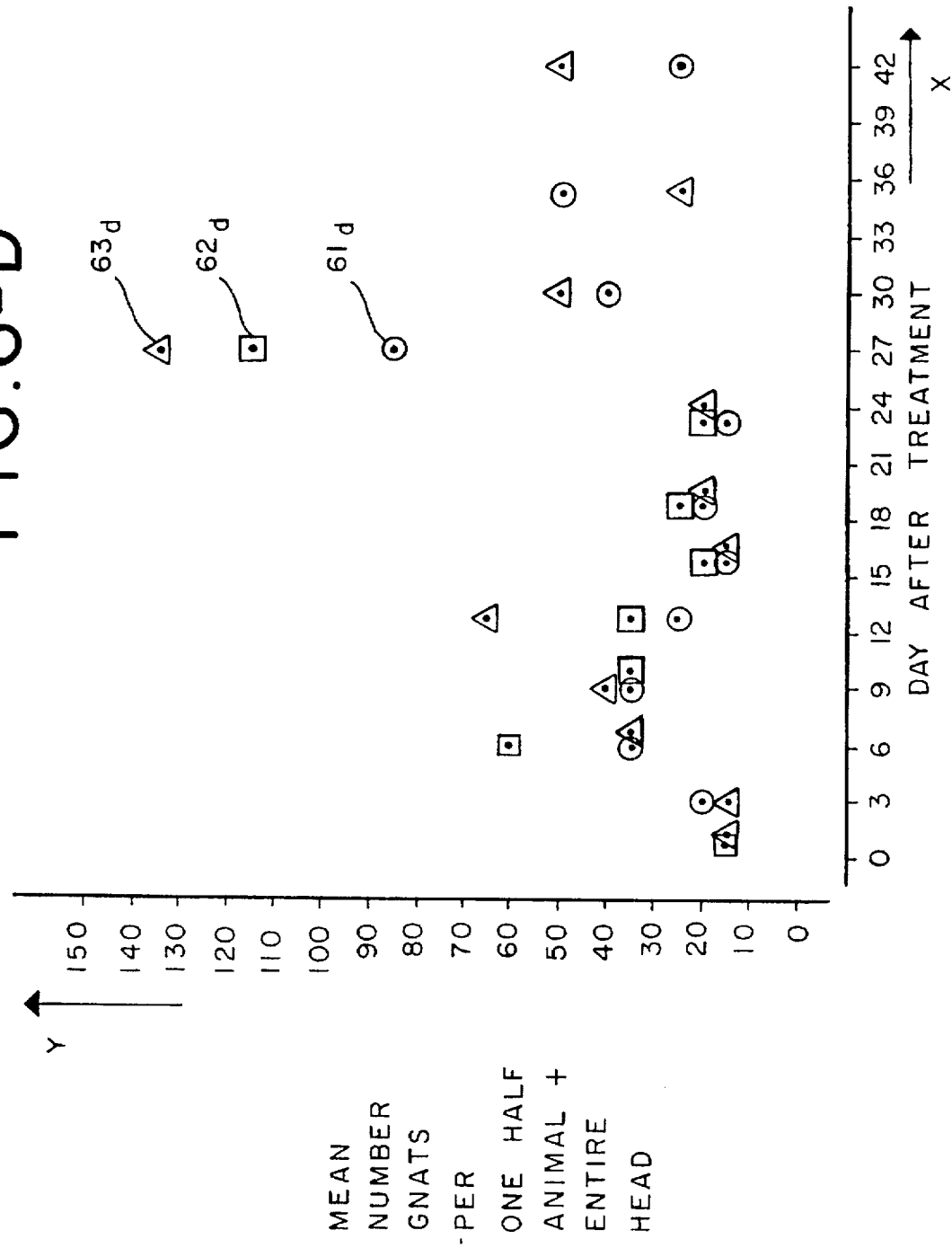

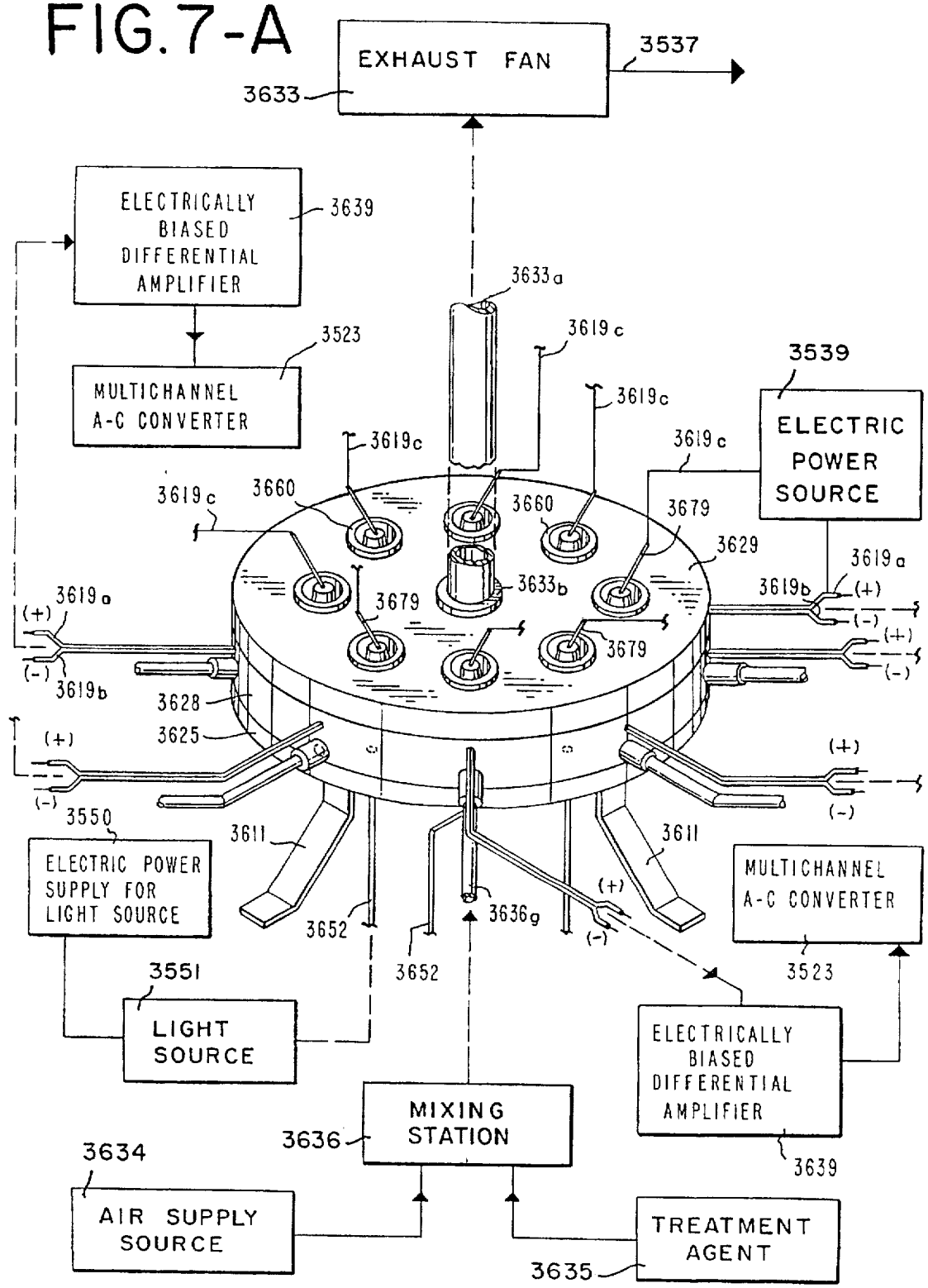

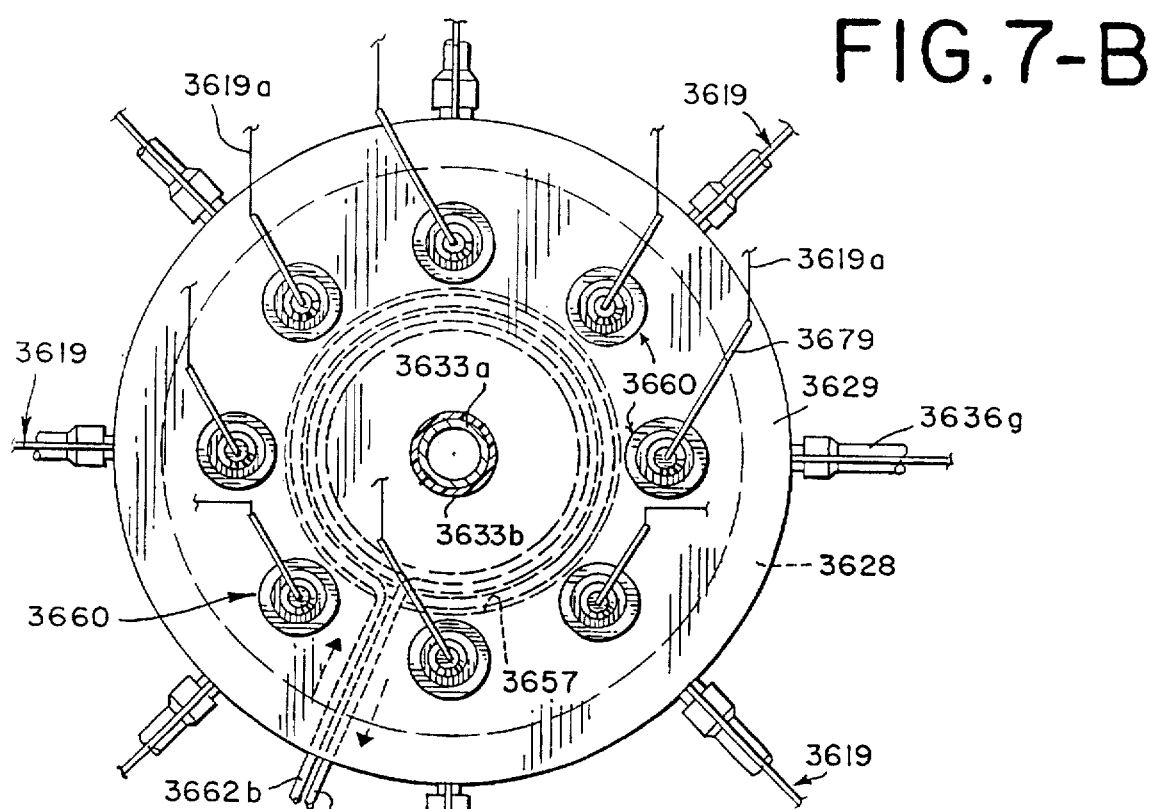
FIG.7-B
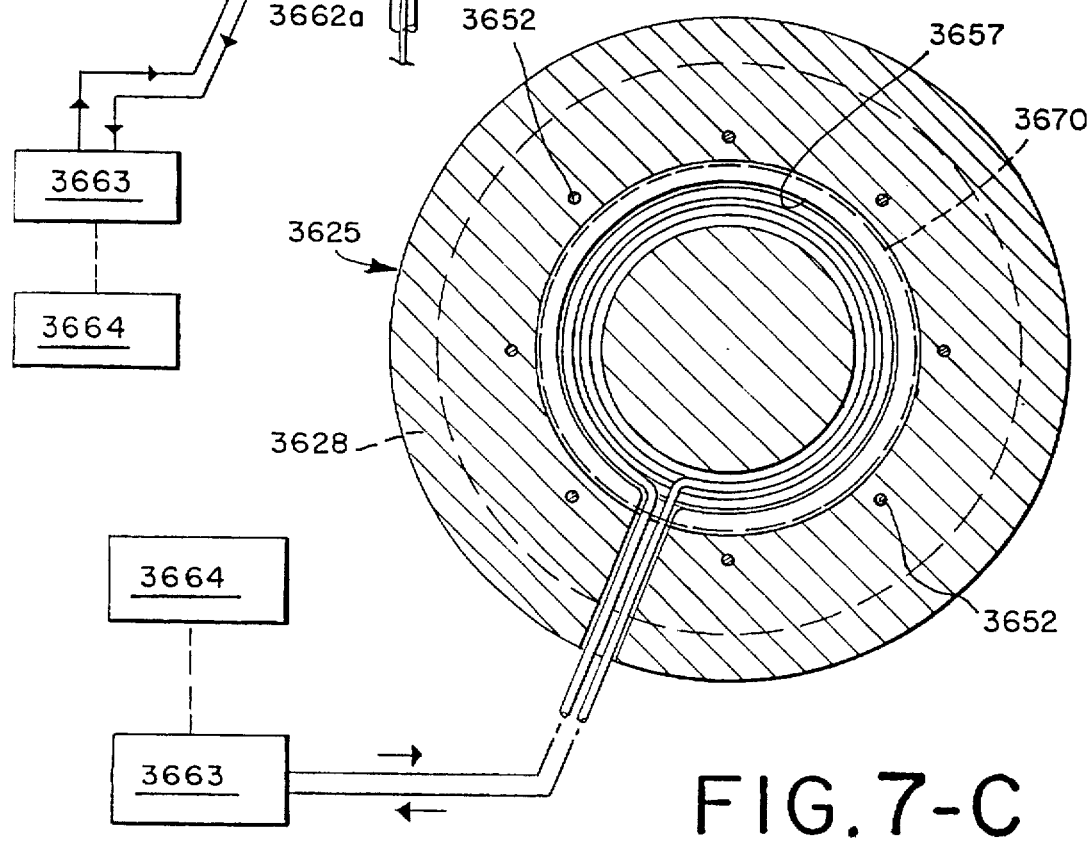
FIG.7-C

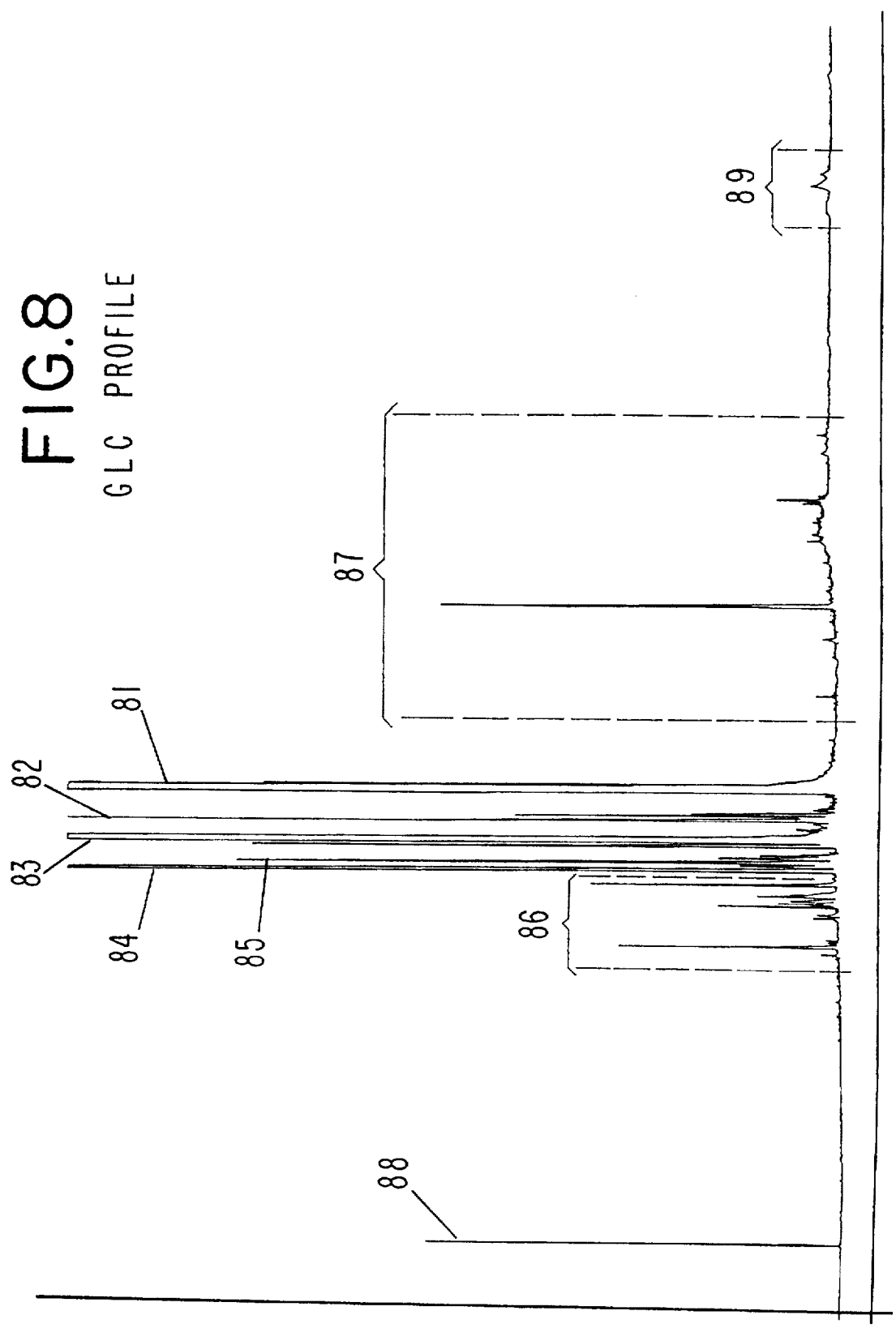

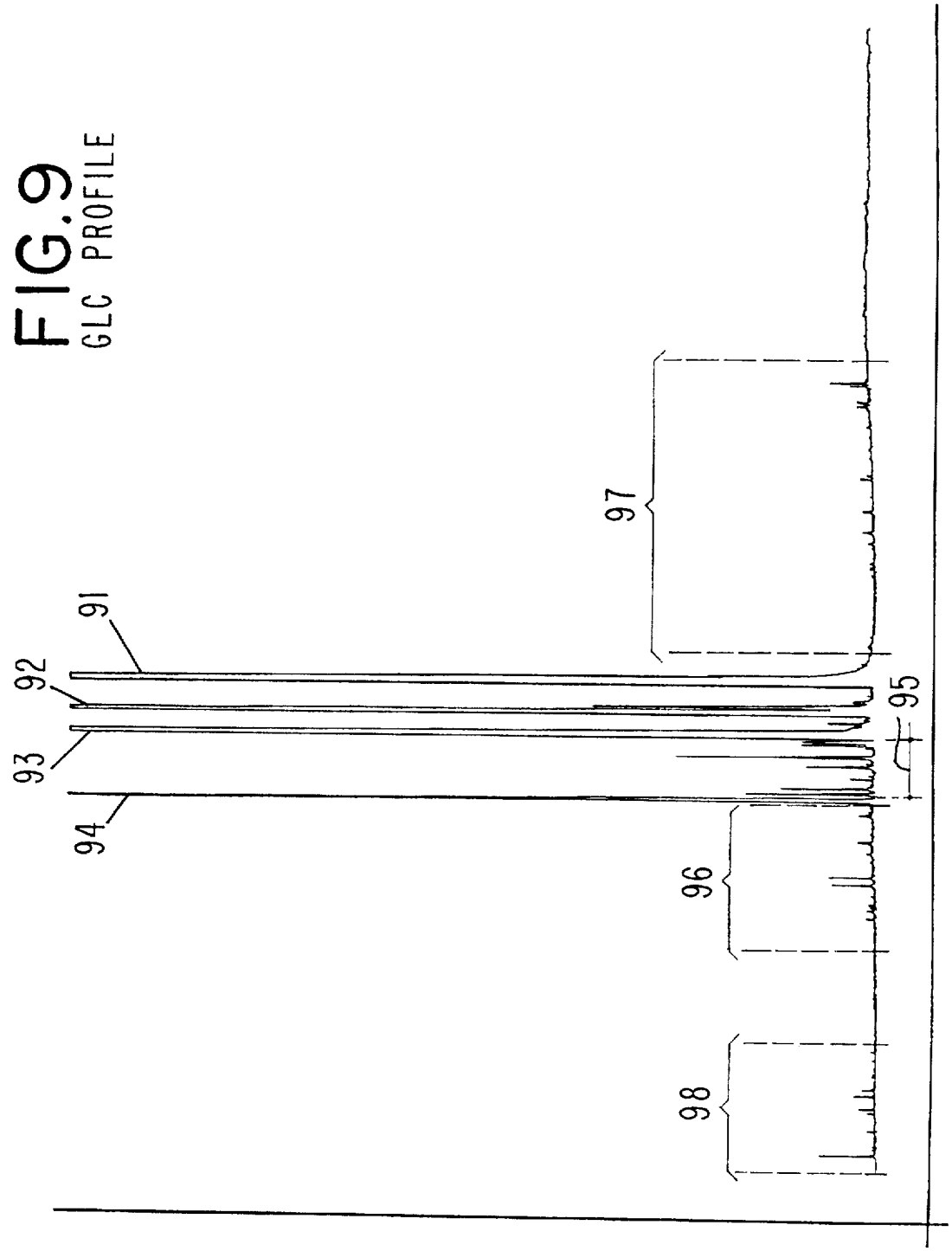

METHOD FOR REPELLING FIRE ANTS AND HORN FLIES AND COMPOSITIONS FOR REPELLING FIRE ANTS AND HORN FLIES AND ACTING AS ANTI-FEEDANTS FOR FIRE ANTS AND HORN FLIES

RELATED UNITED STATES PATENT APPLICATIONS

This application is a Continuation-in-Part of application for U.S. patent, Ser. No. 08/535,670 filed on Sep. 28, 1995 which is a Continuation-in-Part of application for U.S. patent, Ser. No. 08/265,113 filed on Jun. 24, 1994, now abandoned; which, in turn, is a Continuation-in-Part of application for U.S. patent, Ser. No. 07/948,142 filed on Sep. 18, 1992, now abandoned.

Other related applications which evolved from application for U.S. patent, Ser. No. 07/948,142 filed on Sep. 18, 1992, now abandoned, are as follows:

Application for U.S. patent, Ser. No. 08/130,256 filed on Oct. 1, 1993, a Divisional of Ser. No. 07/948,142 filed on Sep. 18, 1992 now abandoned; said application Ser. No. 08/130,256 now U.S. Pat. No. 5,401,500 issued on Mar. 28, 1995;

Application for U.S. patent, Ser. No. 08/241,555 filed on May 12, 1994, a Divisional of Ser. No. 08/130,256 filed on Oct. 1, 1993 now U.S. Pat. No. 5,401,500;

Application for U.S. patent, Ser. No. 08/450,584 filed on May 25, 1995, a Divisional of application for U.S. patent, Ser. No. 08/241,555 filed on May 12, 1994; and Application for U.S. patent, Ser. No. 08/265,219 filed on Sep. 22, 1994, a Continuation-in-Part of application for U.S. patent, Ser. No. 07/948,142 filed on Sep. 18, 1992 now abandoned.

BACKGROUND OF THE INVENTION

Our invention relates to methods of repelling at least one of the insect species, the "red imported fire ant" and/or the "horn fly" from a surface or volume inhabited by such insect species using as a repellent composition materials known as "GERANIOL COEUR™" (Trademark of International Flavors & Fragrances Inc.) defined according to the GLC profiles of FIGS. 8 and 9 and produced according to Examples I and II, infra (also set forth herein as "geraniol-containing compositions" or "geraniol-containing mixtures"). Our invention also relates to the use of such "GERANIOL COEUR™" as insect anti-feedants with respect to the "red imported fire ant" and/or the "horn fly". Accordingly, our invention covers "anti-feedant" compositions for the "red imported fire ant" and the "horn fly".

The "GERANIOL COEUR™" used in our invention comprises:

from about 0 up to about 20% by weight of nerol;

from about 20 up to about 40% by weight of citronellol; and from about 50 up to about 70% by weight of geraniol.

The GERANIOL COEUR™ used as a repellent against such insect species can either be natural GERANIOL COEUR™ or synthetic GERANIOL COEUR™. Such GERANIOL COEUR™ compositions of matter contain a large number of additional chemicals, a number of which may be active in combination with the major components of the GERANIOL COEUR™, namely, the nerol, citronellol and geraniol.

The "red imported fire ant" is known to cause ecological chaos as a result of such insect species causing wholesale deforestation. By the same token, the "horn fly" is a well known insect pest, particularly with respect to domestic agricultural animals such as the cow and horse. Accordingly, a need exists for repelling such insect species, the "red imported fire ant" and the "horn fly", from surfaces or volumes which are inhabited by such insect species.

The properties of the "red imported fire ant" (*Solenopsis invicta* Buren) are described in *ENTOMOLOGY IN HUMAN AND ANIMAL HEALTH*, Seventh Edition, Harwood and James, at pages 430–434 (1977).

Citronellol (both the "d" isomer and the "l" isomer) are described as weak repellents for the yellow-fever mosquito and *Aëdes aegypti* in *CHEMICALS EVALUATED AS INSECTICIDES AND REPELLENTS AT ORLANDO, FLA.*, King, U.S. Department of Agriculture, Agricultural Research, Agriculture Handbook No. 69, at page 120 (Items 3441 and 3442) (published May 1954).

"Geraniol" and various fractions of Java Citronella oil also described as "geraniol" are stated in the King reference at page 179 to be yellow-fever repellents and repellents for *Aëdes aegypti*. Reference is made to Items 5366 ("geraniol"); 5371 ("geraniol, first fraction of Java Citronella oil"); 5372 ("geraniol, second fraction of Java Citronella oil"); 5373 ("geraniol, last fraction of Java Citronella oil"); and 5374 ("geraniol, last fraction, high boiling, Java Citronella oil").

On the other hand, Beroza and Green, *MATERIALS TESTED AS INSECT ATTRACTANTS*, Agriculture Handbook No. 239, Agricultural Research Service, United States Department of Agriculture, June 1963, discloses 3,7-dimethyl octanol-1 having the strucuture:

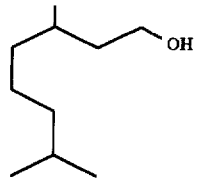

(Item 2883) as being an attractant for the oriental fruit fly, the melon fly and the Mediterranean fruit fly at a level of "1" on a scale of "1–3". The Beroza and Green reference also describes isomers of citronellol and geraniol as having attractancy for various insect species including the pink bollworm and the boll weevil. Thus, Items 2894, 2895 and 2875 for compounds having the structures:

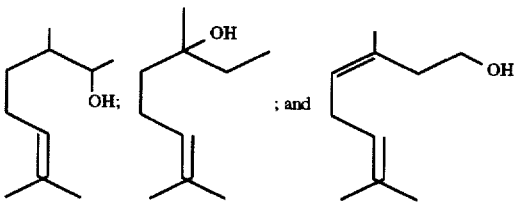

are shown by Beroza and Green to have weak attractancies for the oriental fruit fly, the melon fly, the Mediterranean fruit fly, the Mexican fruit fly, the gypsy moth, drosophila, the pink bollworm and the boll weevil at levels of "1" or "2" on a scale of "1–3".

Nothing in the prior art, however, teaches the repellency against the "red imported fire ant" or the "horn fly" of GERANIOL COEUR™ either natural or synthetic.

THE INVENTION

Our invention is directed to a method for repelling at least one of the insect species:

TABLE I (i) *Haematobia irritans* (Linnaeus) (commonly known as the "horn fly"); and/or
(ii) *Solenopsis invicta* Buren (commonly known as the "red imported fire ant")

from a surface or volume inhabited by at least one of said insect species consisting of the step of applying to said surface or said volume a *Haematobia irritans* (Linnaeus) and/or *Solenopsis invicta* Buren-repelling quantity and concentration of a geraniol-containing composition, GERANIOL COEUR™, natural (shown to be produced in Example I, infra) or synthetic (shown to be produced according to Example II, infra) comprising:

(i) from 0 up to about 20% by weight of nerol;
(ii) from about 20 up to about 40% by weight of citronellol; and
(iii) from about 50 up to about 70% by weight of geraniol defined according to GLC (gas liquid chromatography) profiles of FIGS. 8 and 9 described, infra.

Our invention is also directed to anti-feedant compositions containing such GERANIOL COEUR™ which compositions inhibit the feeding by the above insects, *Haematobia irritans* (Linnaeus) and *Solenopsis invicta* Buren. Accordingly, our invention is directed to a process for inhibiting feeding by the horn fly and the red imported fire ant using the GERANIOL COEUR™ defined, supra.

The GERANIOL COEUR™ natural and GERANIOL COEUR™ synthetic compositions are similar but each has other chemical constituents in addition to the nerol, citronellol and geraniol and these constituents vary from the synthetic to the natural GERANIOL COEUR™. The additional constituents, for example, in the GERANIOL COEUR™, include but are not limited to 3,7-dimethyl octanol-1 having the structure:

(found primarily in the synthetic GERANIOL COEUR™) and β-elemene having the structure:

found in the natural GERANIOL COEUR™. The natural GERANIOL COEUR™'s GLC spectrum is set forth in FIG. 8 and synthetic GERANIOL COEUR™'s GLC spectrum is set forth in FIG. 9.

When discussing a "surface" inhabited by the *Haematobia irritans* (Linnaeus) or inhabited by the *Solenopsis invicta* Buren, such surface can be the skin of an animal such as a cow or the skin of a human being. When discussing the term "volume" inhabited by the *Haematobia irritans* (Linnaeus) or *Solenopsis invicta* Buren, such a volume would be an air space surrounding a cow, for example, or a human being, for example, or the volume could be a room into which a person or animal will enter.

In the event that *Haematobia irritans* (Linnaeus) or the *Solenopsis invicta* Buren is feeding on the skin of the animal, then when coated onto the skin of the animal, the GERANIOL COEUR™ as defined by the GLC spectra of FIGS. 8 and 9 act as anti-feedants. The coating of the GERANIOL COEUR™ onto the skin can be in several forms:

(i) in the form of an aerosol wherein the GERANIOL COEUR™ is incorporated into a standard aerosol formulation at the level of 0.05% up to about 5%; and
(ii) in a non-toxic polymer such as polyvinyl alcohol or polyethylene or polypropylene at the levels of from about 1.0% of GERANIOL COEUR™ up to about 45% by weight of the polymer mixture of GERANIOL COEUR™.

Thus, our invention also contemplates anti-feedant formulations containing a base and incorporated into said base an anti-feedant quantity or concentration of GERANIOL COEUR™, the geraniol-containing mixture, defined according to the GLC spectra of FIGS. 8 or 9 as more specifically described, infra.

The term "citronellol" includes α-citronellol having the structure:

in both its "d" and "l" forms and β-citronellol having the structure:

in both its "d" and "l" forms. GERANIOL COEUR™ natural and GERANIOL COEUR™ synthetic contain, primarily, the compound having the structure:

and, in lesser quantities, the compound having the structure:

The GLC profiles in FIGS. 8 and 9 show both structures. The "d" and "l" forms of a-citronellol can be shown, thusly:

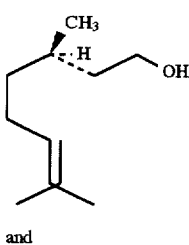

and

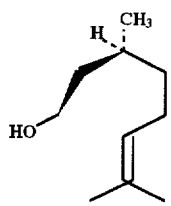

The term "geraniol" in this case is meant to indicate the compound having the structure:

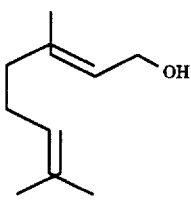

and no other compounds.

The term "nerol" in this application is intended to indicate the compound having the structure:

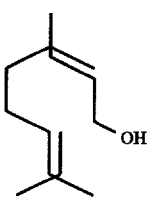

and no other compounds.

Thus, more specifically, our invention covers:

(i) a method for repelling at least one of the insect species, *Haematobia irritans* (Linnaeus) and/or *Solenopsis invicta* Buren, from a surface or volume inhabited by at least one of said insect species consisting of the step of applying to said surface or said volume a *Haematobia irritans* (Linnaeus) and/or *Solenopsis invicta* Buren-repelling quantity and concentration of GERANIOL COEUR™ defined according to one of the spectra of FIG. 8 or FIG. 9 or a mixture thereof; and (ii) an anti-feedant composition for inhibiting the feeding by at least one of the insect species, *Haematobia irritans* (Linnaeus) and/or *Solenopsis invicta* Buren, from a feeding place which can be a skin surface or any other place where *Haematobia irritans* (Linnaeus) or *Solenopsis invicta* Buren feed, such as a food composition containing ingredients which attract, for the purpose of feeding, said *Haematobia irritans* (Linnaeus) or said *Solenopsis invicta* Buren.

The GERANIOL COEUR™ so useful in our invention may be applied in the form of an insect repellent cream, or in the form of an aerosol spray (as indicated, supra) or may be placed into a candle body and may be applied to a volume by means of the use of a burning candle as set forth, for example, at columns 35 and 36 of U.S. Pat. No. 5,175,175 issued on Dec. 29, 1992, the specification for which is incorporated herein by reference. Furthermore, the GERANIOL COEUR™ so useful in our invention may be slowly and controllably released into a volume inhabited by *Haematobia irritans* (Linnaeus) and/or *Solenopsis invicta* Buren by means of first incorporating the GERANIOL COEUR™ (natural or synthetic) into a control release polymer such as microporous polyethylene or microporous polypropylene in accordance with the process set forth at columns 30, 31, 32, 33 and 34 of U.S. Pat. No. 5,175,175 issued on Dec. 29, 1992, the specification for which is incorporated by reference herein.

The GERANIOL COEUR™ so useful in our invention may also be incorporated into a soap base wherein soap articles can be prepared according to the specification of application for U.S. patent, Ser. No. 824,591 filed on Jan. 23, 1992, now U.S. Pat. No. 5,205,065, the specification for which is incorporated by reference herein.

The GERANIOL COEUR™ so useful in our invention may also be combined with other insect-repelling or non-attracting perfume bases whereby the overall composition will repel the *Haematobia irritans* (Linnaeus) as well as the *Solenopsis invicta* Buren. Such insect-repelling bases can be prepared according to the teachings of Application for U.S. patent, Ser. No. 691,635 filed on Apr. 25, 1991 (now abandoned), the specification for which is incorporated by reference herein as well as in accordance with U.S. Pat. No. 5,228,233 issued on Jul. 20, 1993, the specification for which is incorporated by reference herein.

BRIEF DESCRIPTION OF THE DRAWINGS

FIGS. 1A, 1B, 1C and 1D are views of a colony of "red imported fire ants" located on a flat surface surrounded by accessible containers (seven in number) containing control feeding substances as well as test substances including GERANIOL COEUR™ which are determined to be attractants or repellents for the *Solenopsis invicta* Buren.

Thus, FIG. 1A is a top view of the colony surrounded by the test containers containing test substances and also showing the *Solenopsis invicta* Buren species attracted to certain substances and not attracted to other substances.

FIG. 1B is an enlargement of a top view of two of the containers containing test substances shown in FIG. 1A.

FIG. 1C is another enlargement of another top view of two other containers containing test substances of FIG. 1A.

FIG. 1D is a perspective view of the ant colony surrounded by small containers containing testing substances as shown in FIG. 1A.

FIGS. 3A, 3B, 3C and 3D are bar graphs in two or three dimensions showing the feeding rates for the *Solenopsis invicta* Buren ("red imported fire ant") for each of the treated baits and the control as shown in the testing apparatus of FIG. 1A.

Thus, FIG. 3A shows grams consumed of treated bait versus the particular material used in the bait for purposes of testing on the "X" axis. The grams consumed is set forth on the "Y" axis.

FIG. 3B shows the mean visual count of *Solenopsis invicta* Buren ("red imported fire ant") for particular testing material. Thus, the number of fire ants for each of the containers is set forth on the "Y" axis and the particular testing material used is set forth on the "X" axis ("treatment in bait"). The number of ants set forth are ants per quarter hour.

FIG. 3C is a graph in three dimensions showing on the "X" axis the particular treatment used; showing on the "Y" axis the number of ants appearing in each container at a particular point in time; and showing on the "Z" axis ants per quarter hour.

FIG. 3D uses the same data as set forth in FIG. 3C and is a three-dimensional graph for the *Solenopsis invicta* Buren ("red imported fire ant") visual count on the different baits used. On the "X" axis are the number of hours for each of the bar graphs set forth therein. On the "Z" axis are the number of ants found in each container for each point in time and on the "Y" axis are the particular testing materials used.

FIGS. 4A, 4B, 5A, 5B, 5C and 5D relate to tests relating to the use of GERANIOL COEUR™ in repelling "horn flies" (*Haematobia irritans* (Linnaeus)).

FIG. 4A shows the configuration as to the manner in which the testing materials are tested against the (*Haematobia irritans* (Linnaeus) in the field; wherein ear tags are mounted on a cow with the ear tags either containing a control substance or containing a testing substance.

FIG. 4B shows an enlargement of the way that the ear tags containing the testing substance or containing no substance are mounted on the cow in FIG. 4A.

FIG. 5A is a bar graph in three dimensions showing the results of the testing of controls and an attractant and a supposed repellent (GERANIOL COEUR™) when incorporated into ear tags mounted on the cow as shown in FIGS. 4A and 4B. The "Z" axis shows "horn flies" per side of cow. The "X" axis shows the days after treatment. The "Y" axis sets forth the particular treatment material used (or, in fact, when no ear tag is mounted).

FIGS. 6A, 6B, 6C and 6D set forth in two dimensions the results of the testing shown via the bar graph in FIG. 5A. On the "X" axis is shown the number of days after treatment; on the "Y" axis are shown the mean number of flies. The testing against the "horn fly" of FIG. 6A is compared with the same test against houseflies in FIG. 6B; stable flies in FIG. 6C and gnats in FIG. 6D.

FIGS. 5B, 5C and 5D are three-dimensional bar graphs showing testing of various substances including known attractants and possible repellents against "horn flies" (*Haematobia irritans* (Linnaeus)) using the laboratory olfactometer as set forth in schematic form in FIGS. 7A and 7B.

Thus, FIG. 5B shows on the "Z" axis the number of bite seconds; on the "Y" axis, the amount of time that has transpired during the testing; and on the "X" axis, the particular treatment material used. A known attractant, glycerine, is used in the test and, in addition, natural secretion material from cows is compared with GERANIOL COEUR™ (some cows are known to be "naturally repellent"). A replication of the data of FIG. 5B is set forth in FIG. 5C. The data of FIGS. 5B and 5C is combined and is set forth in FIG. 5D.

FIG. 7A is a schematic diagram (blown up for illustration purposes) of olfactometer apparatus useful in ascertaining the efficacy of, inter alia, GERANIOL COEUR™ as a repellent for "horn flies" (*Haematobia irritans* (Linnaeus)) indicating in schematic block flow diagram form the utilization of computer assisted efficacy measuring apparatus; and also showing in block flow diagram form the interrelationship of air and treatment agent mixing station with entry ports for the resulting air-treatment mixture into the olfactometer apparatus. This olfactometer apparatus is described in detail in U.S. Pat. No. 5,175,175 issued on Dec. 29, 1992, the specification for which is incorporated by reference herein.

FIG. 7B is a top view of a base section of an embodiment of the olfactometer apparatus set forth in FIG. 7A showing means for raising the temperature of the insect feeding and/or stimulating means using heating coils.

FIG. 7C is a cut-away cross sectional bottom view of the embodiment of the olfactometer apparatus used in our invention shown, in part, in FIG. 7B showing in detail the location of the heating coil means in the base section of the olfactometer apparatus used for testing.

FIG. 8 is the GLC profile of GERANIOL COEUR™ natural produced according to Example I, infra (Conditions: dual fused silica system programmed from 70°–270° C. at 4° C. per minute).

FIG. 9 is the GLC profile for GERANIOL COEUR™ synthetic produced according to Example II, infra (Conditions: dual fused silica system programmed from 70°–220° C. at 4° C. per minute).

DETAILED DESCRIPTION OF THE DRAWINGS

Figure 2:
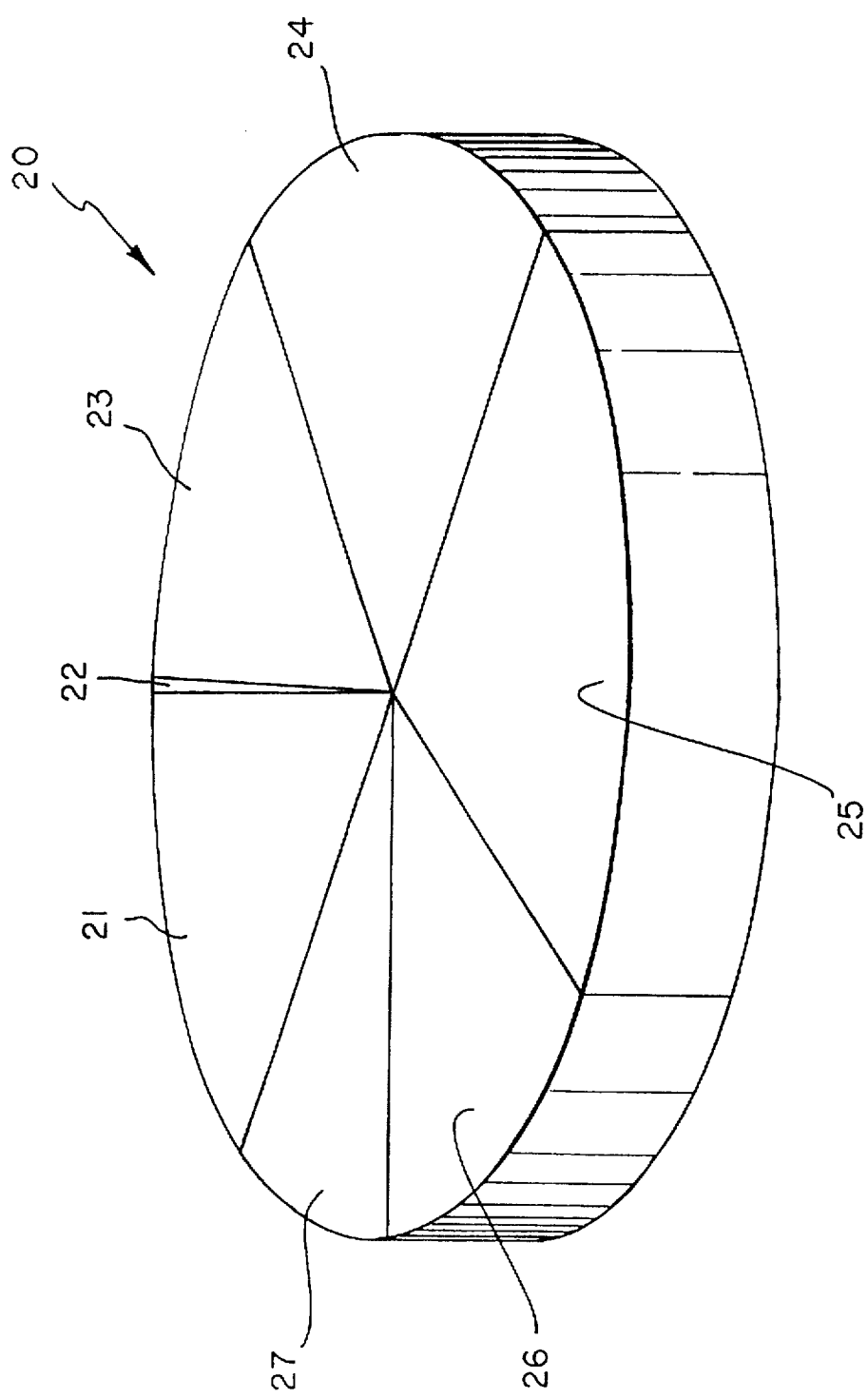
FIG. 2 is a pie graph setting forth the *Solenopsis invicta* Buren ("red imported fire ant") count for each of the test containers containing test substances shown in FIG. 1A. The substances contained in each of the containers are described in detail in THE DETAILED DESCRIPTION OF THE DRAWINGS section, infra.

Referring to FIG. 1A, reference numeral 10 is used to indicate the overall testing system for testing attractancy or repellency as against the "red imported fire ant" (*Solenopsis invicta* Buren). The area indicated by reference numeral 12 is for the fire ant colony. Reference numerals 14a, 14b, 14c, 14d, 14e, 14f and 14g indicate containers containing various "baits" and the actual "baits" are indicated by reference numeral 13. The *Solenopsis invicta* Buren are indicated by reference numeral 15.

The various "baits" are prepared by mixing 0.05 grams of MICRO-CEL®, a synthetic calcium silicate; 0.02 grams of test material; 0.6 grams of corn starch; and 0.4 grams of ground coarse peanut. The total, 1.07 grams, is added to each container with the exception of the control container which only contains a mixture of corn starch and ground coarse peanut (total, 1.00 grams).

Thus, container 14A contains as the test material cetyl alcohol having the structure:

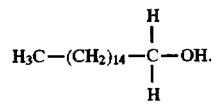

Container 14b contains myristyl myristate having the structure:

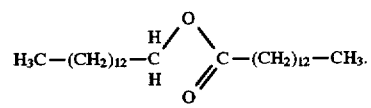

Container 14c contains the "control" (no testing material; just corn starch and ground coarse peanut). Container 14d contains GERANIOL COEUR™ in microporous polyethylene with the amount of GERANIOL COEUR™ based on the microporous polyethylene-containing material being 20% by weight. The GERANIOL COEUR™ is GERANIOL COEUR™ natural defined according to the GLC profile of FIG. 8, described in detail, infra. Container 14e contains cyclodimethicone defined according to the structure:

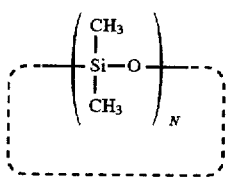

wherein the structure defines a mixture of molecules with:

$3 \leq N \leq 6$ the said cyclodimethicone being a cyclic dimethyl polysiloxane. Container 14f contains propyl paraben having the structure:

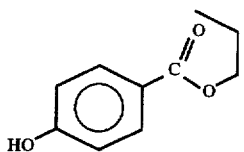

as the test material. Container 14g contains magnesium aluminum silicate having the formula:

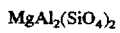

as the test material.

The containers containing test substance are shown in detail in FIGS. 1B and 1C which are enlargements of sections of the drawing of FIG. 1A.

The testing apparatus of FIG. 1A is shown in perspective view in FIG. 1D.

FIG. 2 is a pie chart showing the *Solenopsis invicta* Buren visual count according to the test carried out using the apparatus of FIGS. 1A and 1D. The section of the pie chart indicated by reference numeral 22 is for GERANIOL COEUR™ natural. The section of the pie chart indicated by reference numeral 23 is for the control containing no testing material other than the ground coarse peanut and the starch. The section of the pie chart indicated by reference numeral 24 is for the testing material containing the cetyl alcohol. The section of the pie chart indicated by reference numeral 25 is for the testing material containing the magnesium aluminum silicate. The section of the pie chart indicated by reference numeral 26 is for the testing material containing myristyl myristate. The section of the pie chart indicated by reference numeral 27 is for the testing material containing the propyl paraben as a testing agent. The section of the pie chart indicated by reference numeral 20 is for the testing material containing cyclodimethicone.

Referring to the bar graph of FIG. 3A, grams consumed as set forth on the "Y" axis and the particular treatment is set forth on the "X" axis. This bar graph shows the results of the tests using the apparatus of FIGS. 5A and 5D. The bar graph indicated by reference numeral 31a is for the control containing coarse ground peanut and starch only. The bar graph indicated by reference numeral 32a is for the testing material containing GERANIOL COEUR™ natural. The bar graph indicated by reference numeral 33a is for the testing material containing cyclodimethicone. The bar graph indicated by reference numeral 34a is for the testing material containing magnesium aluminum silicate. The bar graph indicated by reference numeral 35a is for the testing material containing myristyl myristate. The bar graph indicated by reference numeral 36a is for the testing material containing cetyl alcohol. The bar graph indicated by reference numeral 37a is for the testing material containing propyl paraben.

Referring to the bar graph grouping of FIG. 3B with the number of ants on the "Y" axis and the particular treatment in the bait on the "X" axis, the bar graph indicated by reference numeral 31b is for no test material in the testing substance with the exception of the corn starch and the ground coarse peanut. The bar graph indicated by reference numeral 36b is for the testing material containing cetyl alcohol. The bar graph indicated by reference numeral 34b is for the testing material containing magnesium aluminum silicate. The bar graph indicated by reference numeral 35b is for the testing material containing myristyl myristate. The bar graph indicated by the reference numeral 37b is for the testing material containing propyl paraben. The bar graph indicated by reference numeral 33b is for the testing material containing cyclodimethicone. The bar graph indicated by reference numeral 32b is for the testing material containing GERANIOL COEUR™ natural.

Referring to FIG. 3C, the three-dimensional graph showing on the "Y" axis the number of ants; showing on the "Z" axis, the ants per quarter hour in the testing apparatus; and showing on the "X" axis, the particular treatment agent used. The bar graph indicated by reference numeral 32c is for the testing material containing GERANIOL COEUR™ natural. The bar graph indicated by reference numeral 37c is for the testing material containing propyl paraben. The bar graph indicated by reference numeral 35c is for the testing material containing myristyl myristate. The bar graph indicated by reference numeral 36c is for the testing material containing cetyl alcohol. The bar graph indicated by reference numeral 31c is for the control containing only coarse ground peanut and starch. The bar graph indicated by reference numeral 33c is for the testing material containing magnesium aluminum silicate.

Referring to FIG. 3D, the three-dimensional graph showing the number of ants in each of the containers on the "Z" axis; the particular points in time at which the count was taken on the "X" axis and the particular bait treatment on the "Y" axis; the group of bar graphs indicated by reference numeral 301 is for GERANIOL COEUR™ natural in the testing substance. The group of bar graphs indicated by reference numeral 302 is for cyclodimethicone contained in the testing substance. The group of bar graphs indicated by reference numeral 303 is for propyl paraben contained in the testing substance. The group of bar graphs indicated by reference numeral 304 is for myristyl myristate contained in the testing substance. The group of bar graphs indicated by reference numeral 305 is for magnesium aluminum silicate contained in the testing substance. The group of bar graphs indicated by reference numeral 306 is for cetyl alcohol contained in the testing substance. The group of bar graphs indicated by reference numeral 307 is for the control containing only ground coarse peanut and starch.

Referring to FIG. 4A, FIG. 4A is a diagram of a cow having device 40, shown in detail in FIG. 4B. The cow is indicated by reference numeral 49. Now referring to FIG. 4B, the testing material is shown contained in polymer cards 42 attached via attachment device 43 to the ear of cow 49. The overall card with attachment device is set forth by reference numeral 40.

Polyethylene cards are molded, containing 20% by weight of testing material or no testing material at all. The polyethylene cards are molded whereby treatment agent is incorporated directly therein. The treatment agent is either GERANIOL COEUR™ natural as defined according to the GLC spectrum of FIG. 8 or musk ketone having the structure:

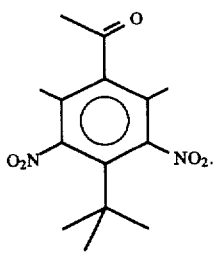

Two cards are used per animal. One treatment card is attached to one ear of the cow and the second card is attached to the second ear of the cow.

Six treated animals had their cards attached and then removed after one week. The cards were brought back from the farm to the laboratory for weighing. Five of the same animals were given a new treatment. One was converted to a control with a new, unused card (and the animal not used in the first trial also got one of the same new, unused control cards). The cards on the three control animals were left on and not returned to the laboratory for weighing. The animals all received 10 ml of viral wart medicine as a follow-up dose on previous treatment when the trial began.

FIG. 5A is a three-dimensional group of bar graphs indicating on the "X" axis the particular day after treatment; on the "Y" axis, the particular treatment agent used or no treatment agent used; and on the "Z" axis, the number of "horn flies" (*Haematobia irritans* (Linnaeus)) per side of animal. The graphs indicated by reference numeral 51a are for cards containing the musk ketone. The bar graphs indicated by reference numeral 52a are for the test materials containing GERANIOL COEUR™ natural. The bar graphs indicated by reference numeral 53a are for the test cards not containing any test material. The bar graphs indicated by reference numeral 54a are for cows not having ear tags attached.

Table II below sets forth the data as set forth in the bar graphs of FIG. 5A.

TABLE II

| Week | Day | Cards Contain Musk Ketone | Cards Contain GERANIOL COEUR ™ Natural | Cards Do Not Contain Test Substance | No Card Used |
|---|---|---|---|---|---|
| 1 | 0 | 106.7 | 118.3 | 100 | 107 |
| 1 | 1 | 48.3 | 48.3 | 80 | 113 |
| 2 | 9 | 20 | 20 | 16 | 132 |
| 2 | 16 | 61.7 | 111.7 | 50 | 180 |
| 3 | 23 | 250 | 200 | 200 | 244 |
| 4 | 30 | 133.3 | 135 | 126.7 | 316 |
| 6 | 35 | 118.3 | 220 | 170 | 191 |

FIGS. 6A, 6B, 6C and 6D are two-dimensional graphs showing the mean number of flies on the "Y" axis versus the day after treatment using the tests described above using the ear tags attached to cows indicated by reference numeral 49.

FIG. 6A is a graph for mean number of "horn flies" per ½ versus days after treatment. The points indicated by reference numeral 61a are for the cards containing musk ketone. The points indicated by reference numeral 62a are for the cards containing GERANIOL COEUR™ natural. The points indicated by reference numeral 63a are for the cards not containing any test substance.

FIG. 6B is a graph of mean number of houseflies (*Musca domestica* L. (Diptera:Muscidae)) versus days after treatment for the cows 49 using the ear tag system 40 as shown in FIGS. 4A and 4B. The points indicated by reference numeral 61b are for the ear tag cards containing 20% by weight of musk ketone. The points indicated by reference numeral 62b are for the cards containing 20% by weight GERANIOL COEUR™ natural. The points indicated by reference numeral 63b are for molded polyethylene cards not containing any test substance.

FIG. 6C is a comparison graph using the cows 49 and the ear tag system 40 showing on the "Y" axis the mean number of stable flies per ½ animal and on the "X" axis the number of days after treatment. The points indicated by reference numeral 61c are for the molded cards containing 20% by weight of musk ketone. The points indicated by reference numeral 62c are for the molded cards containing 20% by weight GERANIOL COEUR™ natural. The points indicated by reference numeral 63c are for the molded cards not containing any test substance.

FIG. 6D is a two-dimensional graph showing the mean number of gnats per ½ animal (and entire head of animals 49) versus number of days after treatment on the "X" axis using the cows 49 and the ear tag system 40 as shown in FIGS. 4A and 4B. The points indicated by reference numeral 61d are for molded cards in the ear tag system 40 containing musk ketone. The points indicated by reference numeral 62d are for molded cards containing GERANIOL COEUR™ natural. The points indicated by reference numeral 63d are for molded cards not containing any test agent.

The data set forth in Tables III and IV is for tests using the laboratory olfactometer described in detail, infra, and set forth in FIGS. 7A and 7B. The results of the tests shown in Tables III and IV are set forth on the three-dimensional bar graphs of FIGS. 5B, 5C and, in summation, in FIG. 5D.

The laboratory olfactometer apparatus of FIGS. 7A, 7B and 7C is operated without engaging electric power supply for light source 3550 (for light source 3551). Thus, the tests are all carried out in the absence of light.

FIG. 7A sets forth in perspective an exploded view of the olfactometer apparatus used in testing the efficacy of, for example, GERANIOL COEUR™ natural or the GERANIOL COEUR™ synthetic against the "horn fly" (*Haematobia irritans* (Linnaeus)).

Air supply source 3634 provides air to mixing station 3636 wherein the air is mixed with treatment agent from treatment agent source 3635 (source of, for example, GERANIOL COEUR™ natural). The resulting mixture passes through tube 3636g (for example) and enters the apparatus through side portals. The entry is through spacer plate 3628 and above base plate 3625. The entry of the air-treatment agent is in a direction parallel to the surface of the base plate 3625. Thus, the base plate 3625 is separated from the spacer plate 3629 for the air-treatment agent (for example, GERANIOL COEUR™ natural or GERANIOL COEUR™ synthetic) lines 3636g. Air exits through line 3633a using exhaust fan 3633. The air exit is indicated by reference numeral 3537.

In several tests, but not in the instant one, simultaneously with the supplying of air and treatment agent from mixing station 3636, light could be supplied from beneath the enclosed insect feeding and/or stimulating means collectively denoted as "IFS" means through light guides 3652 from light source 3551 which could be powered by electric power supply 3550. Air supply from location 3634 and treatment agent from location 3635 is mixed at mixing station 3636 whereupon treatment agent and air in admixture is passed through lines 3636g through portals located in the spacer element 3628 in a direction along a directional vector parallel to the electrical sensing element located directly below the horizontally positioned insect feeding and/or stimulating microporous substantially planar lamina held in place by ring 3660 located on spacer plate 3629 spaced from the base plate 3625 by spacer ring 3628. It should be noted that the spacer plate 3629, spacer rings 3628 and base plate 3625 enclose the entire enclosed insect feeding and/or stimulating means collectively denoted as "IFS" means which have controlled limited access to the external environment surrounding the apparatus and in which the insects to be tested, e.g., "horn flies", houseflies, stable flies and gnats are placed. The apparatus so useful in carrying out the tests for our invention is fully described in U.S. Pat. No. 5,175,175 issued on Dec. 29, 1992, the specification for which is incorporated herein by reference.

FIGS. 7B and 7C show the use of heating elements located in base plate 3625. Thus, in FIG. 7B heating coils 3662a and 3662b are located in base plate 3625. Air and treatment agent are fed into portals located in spacing ring 3628 (but for the purposes of the instant case, no radiation is transmitted through light guides 3652 which are held in place on base plate 3625). Base plate 3625 is spaced at a reasonable distance (e.g., 1.0 inches) using spacer ring 3628 which is sealed in place using silicone seals, for example. In FIG. 7C, a well for the heating coils 3662a and 3662b is contained in base plate 3625 and is indicated by reference numeral 3657. Base plate 3625 is located on a stand which is situated on dampers 3611. The top view of the olfactometer looking down on the face plate 3629 is set forth in FIG. 7B. The reference numeral 3629 refers to the face plate per se. Hidden lines 3662a and 3662b are representations of the heating coils through which heat transfer fluid is supplied through lines 3662a and 3662b (with heated water) using pump 3663, the heat for which is controlled using controller 3664. Coils 3662a and 3662b are preferably covered at cavity 3657 with a heat transfer paste. FIG. 7C is also a top view of the olfactometer with the face plate removed looking directly down on the base plate 3625.

Thus, the materials tested and results thereof are set forth in the description, infra, of FIGS. 5B, 5C and 5D. FIGS. 5B, 5C and 5D are three-dimensional bar graphs showing bite seconds for "horn flies" (*Haematobia irritans* (Linnaeus)); with the "Y" axis showing the points in time at which the measurements are made and with the "X" axis showing the treatment agent. The treatment agents indicated in the bar graphs shown by reference numerals 501b, 502b, 504b, 506b, 507b, 508b, 509b and 510b in FIGS. 5B and by reference numerals 511c, 512c, 5013c, 514c, 506c, 515c, 509c and 516c in FIG. 5C and by reference numerals 509d, 515d, 511d, 512d, 513d and 516d are for secretions obtained from attractant and repellent cows. In fact, the tests for test substances indicated by reference numerals 509d, 515d and 511d are for "attractant" cows; that is, cows that are known to generally attract "horn flies". The secretion test substances indicated by reference numerals 506d, 512d, 513d and 516d are for "repellent" cows; that is, cows that are known to repel "horn flies". The secretion substances were obtained by providing 500 ml of spectra-grade n-hexane. The 500 ml of spectra-grade n-hexane is used as a wash on the side of a cow. The n-hexane is caught in a container. Each n-hexane wash is then evaporated under a nitrogen atmosphere at room temperature and condensed. The resulting condensate is then placed at the rate of 5 micro liters onto an absorbent cellulosic fiber (carboxy methyl cellulose) and the fiber containing the secretion material is then placed in the appropriate part of the olfactometer of FIGS. 7A, 7B and 7C described, supra. By the same token, other testing materials as shown in FIGS. 5B, 5C and 5D, e.g., GERANIOL COEUR™ synthetic (reference numerals 503c, 503d and 503b) and glycerine (reference numerals 505b, 505c and 505d) are also absorbed on the same absorbent material before the test material contained on the absorbent material is placed into the laboratory olfactometer of FIGS. 7A, 7B and 7C.

Thus, referring to FIG. 5B, glycerine (reference numeral 505b) is shown to be an attractant for "horn flies" and GERANIOL COEUR™ synthetic (defined according to the GLC profile of FIG. 9) is shown to be a repellent). Indeed, GERANIOL COEUR™ synthetic (reference numeral 503b) is shown to be a much better repellent than the secretions from the repellent cows 506b, 512b, 513b and 516b.

Referring to FIG. 5C, the GERANIOL COEUR™ synthetic (reference numeral 503c) is shown to be a better repellent than the secretions from the repellent cows 506c, 512c, 513c and 516c. The bar graph indicated by reference numerals 514c and 514d is for the n-hexane wash/secretion material from a "neutral" cow 49 (that is, a cow that is neither "attractant" nor "repellent").

It must be noted that the "standard attractant" is glycerine shown by reference numerals 505d in FIG. 5D, 505c in FIG. 5C and 505b in FIG. 5B.

The following Table III sets forth the data which is shown graphically in FIG. 5B. The numbers contained in each of the columns in the following table set forth the number of bite seconds by the "horn flies" in the olfactometer apparatus of FIGS. 7A, 7B and 7C. Each column is headed by a particular treatment agent. Each row is for a given point in time, e.g., 1 hour, 2 hours, 3 hours and 4 hours.

TABLE III

| TIME (Hours) | COW SECRETION (Reference No. 510b) | ATTRACT-ANT COW SECRE-TION (Reference No. 509b) | COW SECRETION (Reference No. 508b) | COW SECRETION (Reference No. 507b) |
| --- | --- | --- | --- | --- |
| 1.00 | 608.5 | 172.3 | 31.9 | 754.1 |
| 2.00 | 1,127.0 | 570.4 | 371.8 | 861.4 |
| 3.00 | 1,162.3 | 832.8 | 866.4 | 1,191.1 |
| 4.00 | 1,145.5 | 901.8 | 862.3 | 1,045.8 |

| TIME (Hours) | REPELLENT COW SECRETION (Reference No. 506b) | GLYCERINE (Reference No. 505b) | COW SECRETION (Reference No. 504b) |
| --- | --- | --- | --- |
| 1.00 | 65.3 | 1,291.3 | 12.0 |
| 2.00 | 271.7 | 2,349.2 | 340.7 |
| 3.00 | 324.7 | 2,663.6 | 555.5 |
| 4.00 | 443.4 | 2,656.6 | 547.5 |

| TIME (Hours) | GERANIOL COEUR® SYNTHETIC (Reference No. 503b) | COW SECRETION (Reference No. 502b) | COW SECRETION (Reference No. 501b) |
| --- | --- | --- | --- |
| 1.00 | 0.33 | 264.9 | 111.7 |
| 2.00 | 6.98 | 714.2 | 458.4 |
| 3.00 | 8.53 | 1,247.3 | 940.2 |
| 4.00 | 14.37 | 1,402.5 | 1,201.7 |

The following Table IV sets forth the data used in formulating the bar graph of FIG. 5C. The data is as follows:

TABLE IV

| TIME (Hours) | REPELLENT COW SECRETION (Reference No. 516c) | ATTRACTANT COW SECRETION (Reference No. 509c) | ATTRACTANT COW SECRETION (Reference No. 515c) | REPELLENT COW SECRETION (Reference No. 506c) |
|---|---|---|---|---|
| 1.00 | 110.9 | 577.6 | 332.4 | 459.6 |
| 2.00 | 139.5 | 1,156.1 | 915.2 | 849.7 |
| 3.00 | 542.8 | 2,059.1 | 1,678.9 | 1,541.3 |
| 4.00 | 863.6 | 2,323.7 | 2,188.6 | 1,413.7 |

| TIME (Hours) | NEUTRAL COW SECRETION (Reference No. 514c) | GLYCERINE (Reference No. 505c) | GERANIOL COEUR® SECRETION (Reference No. 503c) |
|---|---|---|---|
| 1.00 | 775.2 | 832.8 | 30.9 |
| 2.00 | 841.0 | 1,790.2 | 69.6 |
| 3.00 | 1,651.2 | 2,436.9 | 97.4 |
| 4.00 | 1,732.2 | 2,640.5 | 168.2 |

| TIME (Hours) | REPELLENT COW SECRETION (Reference No. 513c) | REPELLENT COW SECRETION (Reference No. 512c) | ATTRACTANT COW SECRETION (Reference No. 511c) |
|---|---|---|---|
| 1.00 | 376.4 | 207.5 | 416.8 |
| 2.00 | 549.0 | 385.3 | 600.9 |
| 3.00 | 916.8 | 1,032.3 | 1,693.1 |
| 4.00 | 1,120.5 | 1,295.0 | 2,008.8 |

Thus from Table IV which corresponds to the graph of FIG. 5C, it is evident that the GERANIOL COEUR™ synthetic defined according to the GLC profile of FIG. 9 is by far a much better repellent against "horn flies" than is any of the secretions from the known repellent cows.

FIG. 8 is the GLC profile for GERANIOL COEUR™ natural produced according to Example I, infra. The peak indicated by reference numeral 81 is the peak for geraniol having the structure:

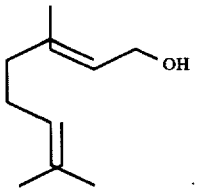

The peak indicated by reference numeral 82 is for nerol having the structure:

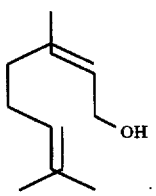

The peak indicated by reference numeral 83 is for α-citronellol having the structure:

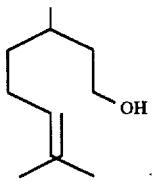

The peaks indicated by reference numerals 84 and 85 are for β-citronellol having the structure:

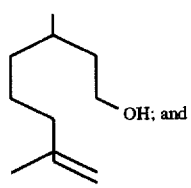

OH; and

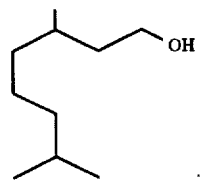

in addition, 3,7-dimethyl octanol-1 having the structure:

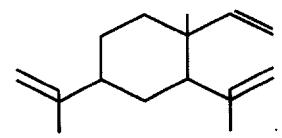

Other materials also are contained in GERANIOL COEUR™ but are of unknown chemical constituency and those are the peaks indicated by reference numerals 86, 87, 88 and 89. Included in the peaks indicated by reference numeral 87 is the compound β-elemene having the structure:

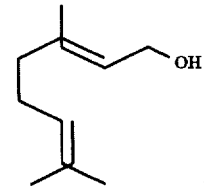

FIG. 9 is the GLC profile for GERANIOL COEUR™ synthetic (produced according to Example II, infra). The peak indicated by reference numeral 91 is the peak for geraniol having the structure:

The peak indicated by reference numeral 92 is the peak for nerol having the structure:

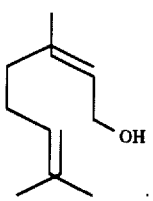

The peak indicated by reference numeral 93 is the peak for α-citronellol having the structure:

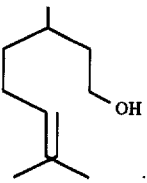

The peak indicated by reference numeral 94 is the peak for 3.7-dimethyl octanol-1 having the structure:

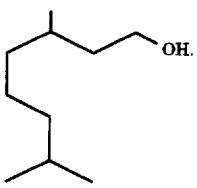

The peaks indicated by reference numerals 95, 96, 97 and 98 are for additional materials contained in GERANIOL COEUR™ synthetic which are of unknown constituency.

\* \* \* \* \*

In place of the carboxy methyl cellulose absorbent material for the material to be tested (e.g., GERANIOL COEUR™ natural or GERANIOL COEUR™ synthetic or glycerine, for example) used in the olfactometer of FIGS. 7A, 7B and 7C, polyethylene pellets (for example, those manufactured by the Chromex Corporation of Brooklyn, N.Y.) can be used. Such polyethylene pellets are microporous polyethylene pellets which are called:

"Innerflow/P75 Polyethylene Pellets".

Indeed, it is preferred to use such microporous polyethylene pellets in carrying out the testing in the olfactometer shown in FIGS. 7A, 7B and 7C.

The following Examples set forth processes for preparing GERANIOL COEUR™ natural (Example I, infra) and GERANIOL COEUR™ synthetic (Example II, infra). All parts are by weight unless otherwise specified.

EXAMPLE I

Preparation of GERANIOL COEUR™ Natural

Palmarosa oil is steam distilled from wild growing, fresh grass of the plant *Cymbopogon Martini*, varietas motia grown in Northeast Katmandu, Nepal. One part of Palmarosa oil is admixed with 4 parts of a 50:50 mixture of sodium hydroxide and methyl alcohol. The resulting mixture is heated at reflux for a period of one hour. 3.5 Parts of anhydrous methanol is then added to the resulting mixture. The resulting mixture is then steam distilled at 100 mm/Hg pressure. GERANIOL COEUR™ natural distills as the middle cut having a refractive index of 1.469–1.475 and a specific gravity at 20°/4° C. of 0.869–0.877. FIG. 8 is the GLC profile for the GERANIOL COEUR™ natural.

EXAMPLE II

Preparation of GERANIOL COEUR™ Synthetic

100 Grams of citronella oil (Java) is admixed with 50 ml of heptane. The resulting mixture is heated on a boiling water bath at 100° C. in a 1 liter flask for a period of one hour. At the end of the one hour period, 8 grams of sodium metal are slowly added to the resulting mixture. The addition of sodium metal takes place over a period of 0.5 hours. The resulting mixture is then filtered. Unreacted sodium is removed and the filtered complex-containing oil is maintained at a temperature of 5° C. for a period of 10 hours. The resulting crystalline product is then filtered and weighs 32 grams. The resulting product is then hydrodistilled in a 2 liter flask with 1.5 liters of water. The hydrodistillate fractions of 100 ml are collected. After separating the aqueous phase from the organic phase, the resulting fractions are analyzed via thin layer chromatography. The fractions are as follows:

| FRACTION NO. | WEIGHT (Grams) | REFRACTIVE INDEX | DENSITY |
|---|---|---|---|
| 1 | 4.5 | 1.456 | 0.8535 |
| 2 | 7.1 | 1.468 | 0.868 |
| 3 | 6.9 | 1.469 | 0.873 |
| 4 | 6.5 | 1.473 | 0.8755 |

Fractions 2, 3 and 4 are then combined to form GERANIOL COEUR™ synthetic. The GLC profile for the GERANIOL COEUR™ synthetic is set forth in FIG. 9.

What is claimed is:

1. A method for inhibiting from feeding at least one of the insect species:

(i) *Haematobia irritans* (Linnaeus) and/or (ii) *Solenopsis invicta* Buren from a surface or volume inhabited by at least one of said insect species and containing an insect species feedant, consisting of the step of applying to said surface or said volume a *Haematobia irritans* (Linnaeus) and/or a *Solenopsis invicta* Buren-anti-feedant quantity and concentration of a geraniol-containing mixture comprising:

(i) from 0 to about 20% by weight of nerol having the structure:

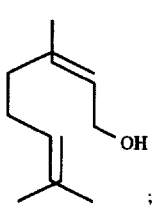

(ii) from about 20 up to about 40% by weight of citronellol having the structure:

(iii) from about 50 up to about 70% by weight of geraniol having the structure:

defined according to the GLC profiles of FIG. 8 or of FIG. 9 and having a refractive index in the range of from 1.456 up to 1.475 and a density in the range of from 0.8535 up to 0.877.

2. The method of claim 1 wherein the geraniol-containing composition is defined according to the GLC profile of FIG. 8 and having a refractive index in the range of from 1.469 up to 1.475 and a density in the range of from 0.869 up to 0.877.

3. The method of claim 1 wherein the geraniol-containing composition is defined according to the GLC profile of FIG. 9 and having a refractive index in the range of from 1.456 up to 1.473 and a density in the range of from 0.8535 up to 0.8755.

4. A method for inhibiting *Haematobia irritans* (Linnaeus) from feeding at a surface or in a volume inhabited by said *Haematobia irritans* (Linnaeus) and containing a feedant, consisting of the step of applying to said surface or said volume a *Haematobia irritans* (Linnaeus)-anti-feedant quantity and concentration of a geraniol-containing composition defined according to the GLC spectrum of FIG. 8 and having a refractive index in the range of from 1.469 up to 1.475 and a density in the range of from 0.869 up to 0.877.

5. A method for inhibiting the insect species *Haematobia irritans* (Linnaeus) from feeding at a surface or in a volume inhabited by said *Haematobia irritans* (Linnaeus) and containing a feedant for said insect species, consisting of the step of applying to said surface or said volume a *Haematobia irritans* (Linnaeus)-anti-feedant quantity and concentration of a geraniol-containing composition defined according to the GLC spectrum of FIG. 9 and having a refractive index in the range of from 1.456 up to 1.473 and a density in the range of from 0.8535 up to 0.8755.

6. A method for inhibiting *Solenopsis invicta* Buren from feeding at a surface or in a volume inhabited by said *Solenopsis invicta* Buren and containing a feedant for said *Solenopsis invicta* Buren, consisting of the step of applying to said surface or said volume a *Solenopsis invicta* Buren-anti-feedant quantity and concentration of a geraniol-containing composition defined according to the GLC profile of FIG. 8 and having a refractive index in the range of from 1.469 up to 1.475 and a density in the range of from 0.869 up to 0.877.

7. A method for inhibiting *Solenopsis invicta* Buren from feeding at a surface or in a volume inhabited by said *Solenopsis invicta* Buren and containing a feedant for said *Solenopsis invicta* Buren, consisting of the step of applying to said surface or said volume a *Solenopsis invicta* Buren-anti-feedant quantity and concentration of a geraniol-containing composition defined according to the GLC spectrum of FIG. 9 and having a refractive index in the range of from 1.456 up to 1.473 and a density in the range of from 0.8535 up to 0.8755.

8. The method of claim 1 wherein the geraniol-containing composition is contained in a microporous polymer.

9. The method of claim 2 wherein the geraniol-containing composition is contained in a microporous polymer.

10. The method of claim 3 wherein the geraniol-containing composition is contained in a microporous polymer.

* * * * *